US006106825A

United States Patent [19]

Moyer et al.

[11] Patent Number: 6,106,825

[45] Date of Patent: Aug. 22, 2000

[54] ENTOMOPOXVIRUS-VERTEBRATE GENE DELIVERY VECTOR AND METHOD

[75] Inventors: Richard W. Moyer; Yi Li; Richard L. Hall, all of Gainesville, Fla.

[73] Assignee: University of Florida, Gainesville, Fla.

[21] Appl. No.: 08/852,629

[22] Filed: May 7, 1997

[51] Int. Cl.[7] ............................ A01N 63/00; C12N 7/01; C12N 5/10; C12N 15/63

[52] U.S. Cl. .................... 424/93.2; 424/93.1; 435/235.1; 435/325; 435/456; 435/457; 514/44

[58] Field of Search ................................ 435/235.1, 325, 435/320.1, 172.3, 456, 457; 514/44; 424/93.1, 93.21, 93.2

[56] References Cited

U.S. PATENT DOCUMENTS

| | | | |
|---|---|---|---|
| 5,174,993 | 12/1992 | Paoletti | 424/89 |
| 5,338,679 | 8/1994 | Yuen et al. | 435/235.1 |
| 5,476,781 | 12/1995 | Moyer et al. | 435/240.2 |

FOREIGN PATENT DOCUMENTS

| | | |
|---|---|---|
| 8903429 | 8/1988 | WIPO . |
| 9303144 | 8/1992 | WIPO . |
| 9214818 | 9/1992 | WIPO . |
| 9325666 | 12/1993 | WIPO . |
| 9413812 | 6/1994 | WIPO . |
| 9609074 | 9/1995 | WIPO . |

OTHER PUBLICATIONS

Verma et al. Gene therapy—promises, problems and prospects. Nature, vol. 389, pp. 239–242, Sep. 18, 1997.

Li, Yi, R.L. Hall, R.W. Moyer (1997) “Transient, Nonlethal Expression of Genes in Vertebrate Cells by Recombinant Entomopoxviruses” Journal of Virology 71(12):9557–9562.

Arif, Basil M., (1995) “Recent Advances in the Molecular Biology of Entomopoxviruses” Journal of General Virology 76:1–13.

Moyer, Richard W., (1994) “Entomopoxviruses” In R.G. Webster and A. Granoff (eds.) Encyclopedia of Virology pp. 392–298, Academic Press, Ltd., London.

Ganados, Robert R., (1981) “Entomopoxvirus Infection in Insects” In E.W. Davidson (ed.) Pathogenesis of Invertebrate Microbial Diseases, pp. 101–126. Allanheld, Osmun & Co., Totowa, NJ.

Tine, A.J., et al., (Sep., 1996) “NYVAC–Pf7: A Poxvirus-Vectored, Multiantigen, Multistage Vaccine Candidate for *Plasmodium falciparum* Malaria” Infection and Immunity pp. 3833–3844.

Lanridge, W.H.R., (1983) “Detection of *Amsacta moorei* Entomopoxvirus and Vaccinia Proteins in Cell Cultures Restrictive for Poxvirus Multiplication” Journal of Invertebrate Pathology 42:77–82.

Hall, R.L., et al., (1996) “The *Amsacta moorei* Entomopoxvirus Spheroidin Gene Is Improperly Transcribed in Vertebrate Poxviruses” Virology 224:427–436.

Palmer, Christopher P., et al., (1995) “Genetic Modification of an Entomopoxvirus: Deletion of the Spheroidin Gene does not Affect Virus Replication in Vitro.” Journal of General Virology 76:15–23.

Hoffman, Christian, et al., (Oct. 1995) “Efficient Gene Transfer into Human Hepatocytes by Baculovirus Vectors” Proc. Nat'l. Acad. Sci. 92:10099–10103.

Boyce, Frederick M., Nancy L. R. Bucher, (Mar. 1996) “Baculovirus–Mediated Gene Transfer into Mammalian Cells” Proc. Nat'l. Acad. Sci. 93:2348–2352.

*Primary Examiner*—Deborah J. Clark
*Attorney, Agent, or Firm*—Saliwanchik, Lloyd & Saliwanchik

[57] ABSTRACT

This invention provides recombinant entomopoxvirus as a novel vector and method of using such vector for delivery and expression of genes of biological significance to vertebrate cells, including human cells. This invention includes the use of an early entomopoxvirus or like gene promoter to drive the expression of an heterologous gene product in a vertebrate cell infected with the recombinant entomopoxvirus vector. We have discovered that, while the entomopoxvirus vector of this invention does not replicate in the vertebrate cell, it enters vertebrate cell cytoplasm and achieves expression of an heterologous gene inserted into the rEPV without causing cytopathic or cytotoxic effects. We further provide a method for expression of the heterologous gene under control of late, strong entomopoxvirus gene promoters, vertebrate gene or viral promoters, and for stable integration of the heterologous gene delivered by the rEPV into the vertebrate cell.

25 Claims, 7 Drawing Sheets

ENTOMOPOXVIRUS-VERTEBRATE GENE DELIVERY VECTOR AND METHOD

This invention was made with government support under NSF Grant No. IBN-9406571. The government has certain rights in this invention.

BACKGROUND OF THE INVENTION

1. Field of the Invention

This invention provides a novel vector and method of using such vector, comprising recombinant entomopoxviruses, for delivery of genes of biological significance for expression in vertebrates, including humans.

2. Background

A number of heterologous gene delivery systems have been evaluated in vertebrate hosts. These include vaccinia virus recombinants, recombinant retroviral vectors, naked DNA vectors, biolistic gene delivery, or delivery of recombinant DNA constructs via liposomes or other transfection enhancing means. Each of these known methods have advantages and disadvantages. Accordingly, there is an ongoing need in the art for new gene delivery vectors and methods, and this invention provides a further option for those skilled in the art, namely, the use of recombinant entomopoxvirus vectors for delivery of heterologous genes for expression in vertebrate cells.

To date, there does not appear to have been any disclosure or suggestion in the art that entomopoxviruses (EPVs) could be used to deliver and express genes of biological significance in vertebrate hosts. EPVs are poxviruses of insects and the most distant relatives of the more commonly studied vertebrate orthopoxviruses vaccinia, (VV) and cowpox virus (CPV). Orthopoxviruses are the only mammalian DNA viruses which replicate in the cytoplasm. To achieve this, the virus must synthesize all the enzymes necessary to transcribe and replicate the viral DNA within the cytoplasm.

Poxviruses comprise two sub-families, the Chordopoxvirinae (vertebrate viruses) and the Entomopoxvirinae (insect viruses; Arif, 1995; Moyer, 1994). Vaccinia is the prototypic vertebrate poxvirus. The Entomopoxvirinae (EPVs) were only recently discovered (1963) but are now known to be distributed world-wide and productively infect primarily Orthoptera, Diptera, Coleoptera and Lepidoptera orders of insects. The prototypical EPV is the lepidopteran virus isolated from*Amsacta moorei* (AmEPV) which grows well in cultured insect cells.

The orthopoxviruses and the EPVs have some features in common, yet are quite distinct. Similarities include: morphology, a large linear double stranded genome (190 kb for VV, 225 kb for AmEPV), common sequence motifs (that in the vertebrate poxviruses are associated with transcriptional regulation), non-spliced transcripts, a cytoplasmic site of replication, and production of cytopathic effects in their natural host cells. Differences include: the G+C content of the viral DNA (37% for VV, but only 18% for AMEPV); optimal growth temperatures (26° C. for AmEPV, 37° C. for VV); and host range (AmEPV does not replicate in vertebrate cells and VV does not replicate in insect cells), although both viruses enter their non-permissive cells, (Langridge, 1983, and FIG. 1 herein). It has recently been observed that poxvirus promoters are not universally conserved as there are at least some late AmEPV promoters which are specific for the insect environment (Hall et al., 1996).

In U.S. Pat. No. 5,476,781, and foreign equivalents thereof (WO 92/14818 and WO 94/13812), entomopoxvirus spheroidin or thymidine kinase sequences and non-entomopoxvirus vectors containing these sequences were disclosed. However, these references neither disclose nor suggest a recombinant entomopoxvirus that is capable of acting as a vector for expression of an heterologous gene in a vertebrate cell. If anything, these publications tend to teach away from such a conclusion in that it is clearly stated that the entomopoxviruses are unable to replicate in vertebrate cells. Therefore, from these publications, one of ordinary skill in the art would be taught that a viral vector containing entomopoxvirus sequences would need to be a virus other than an entomopoxvirus to be useful for delivery of heterologous sequences to vertebrate or mammalian cells in vitro.

Entomopoxviruses are only known to productively infect and kill insects (Granados, 1981). No changes in cellular morphology by phase contrast microscopy were reported when *Amsacta moorei* entomopoxvirus (AMEPV, a virus isolated originally from the red hairy caterpillar) is used to infect mouse L-929 cells at a multiplicity of infection (m.o.i.) of 10 plaque forming units (p.f.u.) per cell.

Langridge (1983) demonstrated that AmEPV was able to enter a mammalian cell, but was reported to be unable to replicate or express its own proteins, as the gross $^{35}$S-methionine pulse-labeled protein pattern of AmEPV-inoculated L-929 cells was identical to the protein pattern from uninoculated cells.

Granados (1981) reported that there was no evidence of a productive AmEPV infection in a human (HeLa) cell line, and that the host range of AmEPV is restricted to insects. In a typical vertebrate poxvirus infection of a vertebrate cell, there is a rapid shut-down of host cell protein synthesis. However, as disclosed herein, vertebrate cells contacted with AmEPV failed to demonstrate this shut-down in protein expression.

In U.S. Pat. No. 5,338,679, Yuen and Arif disclosed vertebrate poxvirus expression vectors capable of expressing heterologous genes under the control of an entomopoxvirus gene promoter. The patentees mistakenly believed that the entomopoxvirus promoter they were using was the spheroidin promoter, but have since publicly acknowledged that the promoter they used was in fact the entomopoxvirus fusolin promoter. Thus, the Yuen and Arif patent discloses vertebrate poxviruses wherein expression of the heterologous gene is driven by what turns out to be the entomopoxvirus fusolin promoter. Accordingly, while this publication established the possibility of using an entomopoxvirus promoter to drive expression of a gene in a vertebrate, there was no disclosure or suggestion that entomopoxvirus itself could be used as the recombinant viral vector for delivery of and subsequent heterologous gene expression in a vertebrate system.

Paoletti, U.S. Pat. No. 5,174,993, disclosed a recombinant avipox virus in which an early entomopoxvirus promoter, referred to in that patent and herein as the AmEPV 42k promoter or as the EPV early strong promoter (esp), was used to drive expression of heterologous genes in a vertebrate viral vector. Thus, like the Yuen and Arif patent, this patent establishes the possibility of using an entomopoxvirus promoter to drive expression of a gene in a vertebrate. However, also like the Yuen and Arif patent, there is no disclosure or suggestion that entomopoxvirus itself could be used as the recombinant viral vector for delivery and subsequent heterologous gene expression in a vertebrate system.

Tine et al., (1996) disclosed an expression system in which the EPV 42k promoter was used to prepare a malaria vaccine in a recombinant vaccinia virus vector.

Dall et al., WO 93/25666, and EP 646172, published on Apr. 5, 1995, disclosed recombinant entomopoxviruses for use in the control of insect pests or for production of recombinant proteins in cell culture. This publication notes that an advantage of EPV's for recombinant production of proteins is that the "EPV's do not necessarily cause lysis of the infected cell, thereby offering potential for long term persistent infection of large scale cell culture." However, there is no disclosure or suggestion that the disclosed recombinant entomopoxviruses could be used in vitro in vertebrate cells or in vivo as a vector for delivery and subsequent heterologous gene expression in vertebrates.

Palmer et al. (1995), as with the Dall et al. PCT publication, disclosed genetic modification of various entomopoxvirus genomes. However, there is no disclosure or suggestion that the thus modified entomopoxviruses could serve as a recombinant viral vector for delivery and subsequent expression of an heterologous gene in a vertebrate.

Several publications have emerged showing that baculovirus, an insect virus unrelated to the entomopoxviruses, is able to deliver genes for expression in vertebrate cells (Hofman et al., 1995; Boyce and Bucher, 1996). However, the baculovirus system depends on the vertebrate cell's transcriptional machinery for heterologous gene expression. In addition, these references teach nothing with respect to EPV interactions with vertebrate cells and therefore stand apart from the instant disclosure of recombinant entomopoxviruses for delivery and subsequent expression of foreign genes in vertebrate cells.

BRIEF SUMMARY OF THE INVENTION

This invention provides novel vectors and a method of using such vectors comprising recombinant entomopoxviruses for delivery and expression of genes of biological significance to vertebrates, including humans. This invention includes the use of an early entomopoxvirus or like gene promoter to drive the expression of an heterologous gene product in a recombinant entomopoxvirus (rEPV) vector. We have discovered that, while the entomopoxvirus vector of this invention is apparently able to enter into the vertebrate cell cytoplasm and achieve expression of the heterologous gene, the virus itself does not appear to be able to replicate in the cell and, perhaps most importantly, does not appear to be cytotoxic or lead to cell death. Baculovirus, which has been used as a live recombinant vector for delivery of genes into vertebrate cells, depends on the cellular machinery for transcription. In addition, baculovirus enters the nucleus of the cell, raising concerns about the possibility of chromosomal integration and disruption of normal genomic expression.

We demonstrate herein that heterologous genes under the control of EPV early gene promoters, or promoters which are recognized by the EPV transcriptional factors present in the EPV viral particle and therefore behave like early EPV gene promoters, or promoters recognized by the vertebrate cell's transcriptional apparatus when the rEPV is directed to enter the vertebrate cell nucleus, are expressed when vertebrate cells are contacted with the rEPV, even though EPV does not productively infect vertebrate cells (i.e., fails to replicate and fails to express most of the entomopoxvirus specific proteins). EPV genes under control of late promoters are not expressed. The infected cells survive, and the protein expression is limited by the stability of the EPV-transcriptional apparatus, which remains in the cellular cytoplasm.

We prepared a series of AmEPV-lacZ recombinants wherein the lacZ gene is regulated by either late (the AmEPV spheroidin or cowpoxvirus A-type inclusion body (ATI)) promoters or early promoters (the AmEPV early strong promoter, esp, or *Melolontha melolontha* MmEPV fusolin viral promoters). When the recombinants were used to infect vertebrate cells, β-galactosidase expression occurred (>30% cells) when the lacZ was regulated by either the fusolin or esp promoters but not where lacZ was regulated by the late spheroidin or ATI promoters. Therefore, we have found that recombinant EPV enters vertebrate cells, undergoes at least partial uncoating and early, but not late, viral genes are expressed. When rEPV encoding the jellyfish green fluorescent protein (gfp) under control of the esp promoter or the fusolin promoter was used to infect vertebrate cells, single fluorescent cells were observed which continued to divide over a period of several days, ultimately forming fluorescent cell clusters, demonstrating that vertebrate cells survive infection and continue to grow (see FIG. 6). Therefore, based on these findings, we conclude that entomopoxviruses may be used as efficient, non-toxic vectors for gene delivery to vertebrate cells for transient expression.

We demonstrate that rEPV encoding the β-gal gene driven by an early entomopoxvirus promoter is capable of driving expression of β-galactosidase upon infection of a vertebrate cell line in vitro. FIG. 1 shows the expression of this enzyme and evidence that the entomopoxvirus is not cytotoxic. This benign character of the virus is of tremendous value as it can be envisioned that, in vivo, the host organism will not be required to mount an immune response against this virus or cells in which it becomes housed. The key here is that only the early class of viral proteins are synthesized. As the late viral proteins are not efficiently synthesized in rEPV-infected vertebrate cells, the level of viral structural proteins is minimal or non-existent in this system. Hence this system provides for very low levels of foreign antigens against which the vertebrate immune system is required to react.

As a result of these features, one object of this invention is to provide an entomopoxvirus vector for use as a vertebrate gene delivery vehicle.

Other objects include:

Provision of a non-replicating vector for cytoplasmic expression of heterologous genes in vertebrate cells;

Establishment of a method for use of entomopoxviruses to deliver genes for transient or stable expression in vertebrates;

Establishment of methods for in situ expression of foreign genes when rEPV vectors are introduced into the lung, liver or other organ;

Construction of high-level entomopoxvirus vertebrate expression vectors by insertion of an inducible bacteriophage T7/lacZ cassette or analogous expression cassettes into the entomopoxvirus genome.

Provision of a novel vaccine vector wherein a recombinant EPV vector is used to deliver an effective amount of an immuno-stimulatory antigen.

Other objects and features of this invention will become apparent from a review of the complete disclosure and the appended claims.

Panel A— Uninfected CV-1 (African green monkey) cells.

Panel B— CV-1 cells infected with recombinant AmEPV having lacZ expression driven by the ATI promoter (ATIlacZ).

Panel C— CV-1 cells infected with recombinant AmEPV having lacZ expression driven by the EPV spheroidin promoter (sphlacZ).

Panel D— CV-1 cells infected with recombinant AmEPV having lacZ expression driven by the EPV fus promoter (fus-lacZ).

Panel E— CV-1 cells infected with recombinant AMEPV having lacZ expression driven by the EPV 42k promoter (42klacZ).

Panel F— human liver cells (Huh-7) infected with recombinant AmEPV having lacZ expression driven by the EPV esp promoter (esp-lacZ).

Figure 1A:
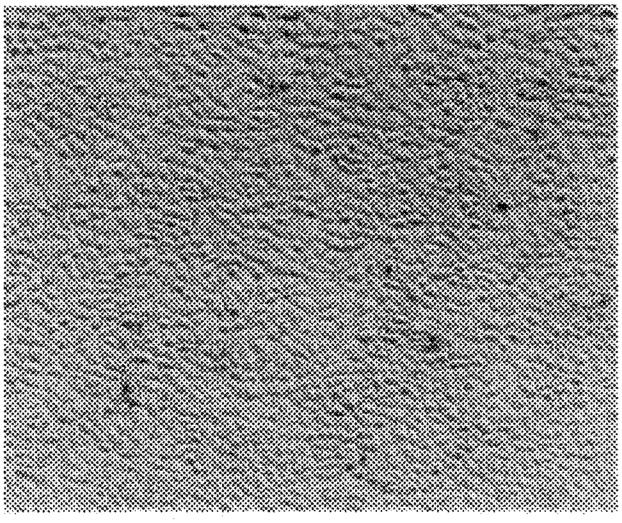
FIG. 1(A–F) shows a series of cells infected with different viral recombinants, where all cells were stained 24 hours post-infection with the indicated rEPV.
Figure 1B:
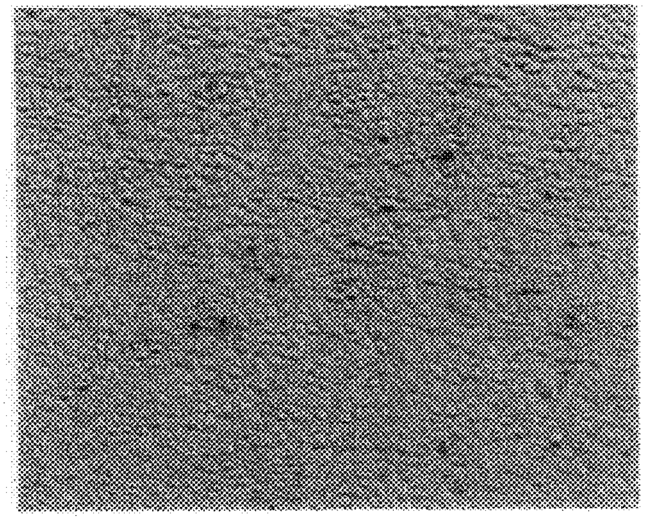
Figure 1C:
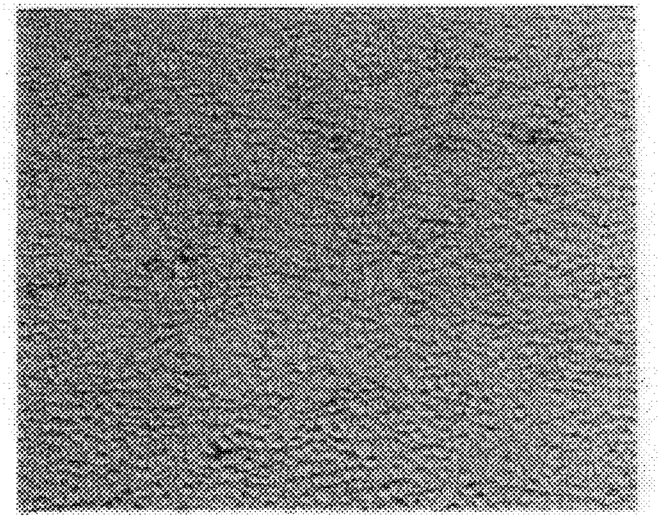
Figure 1D:
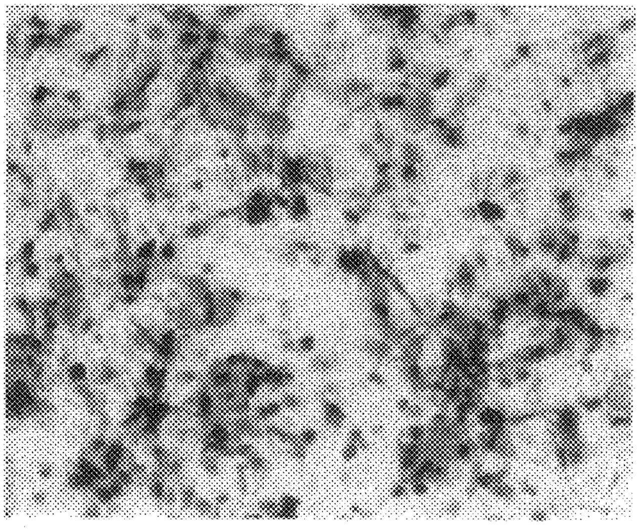
Figure 1E:
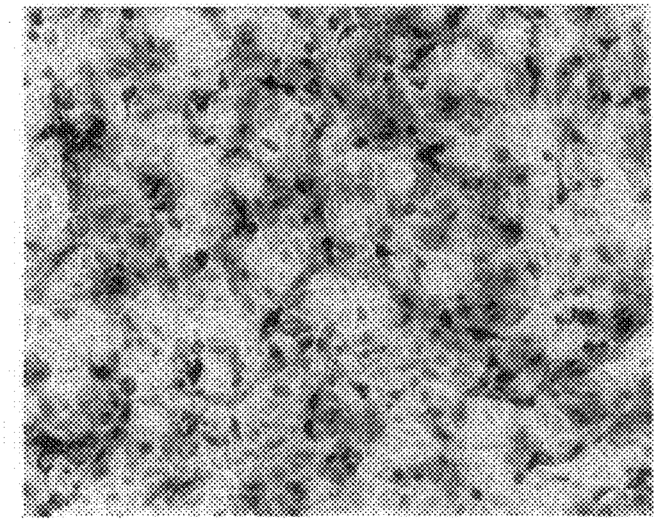
Figure 1F:
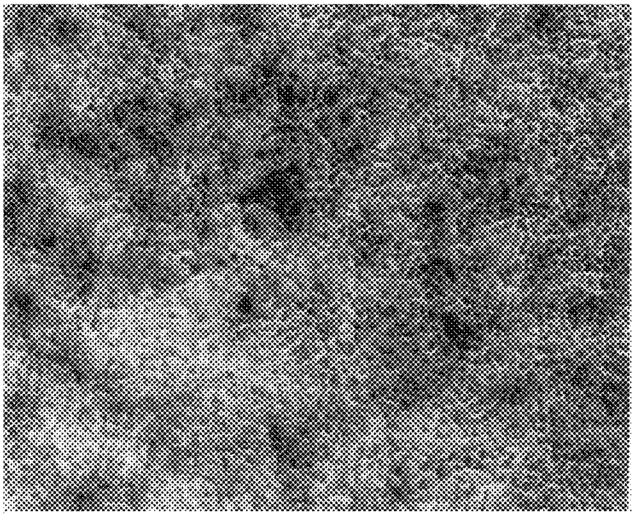
Figure 2A:
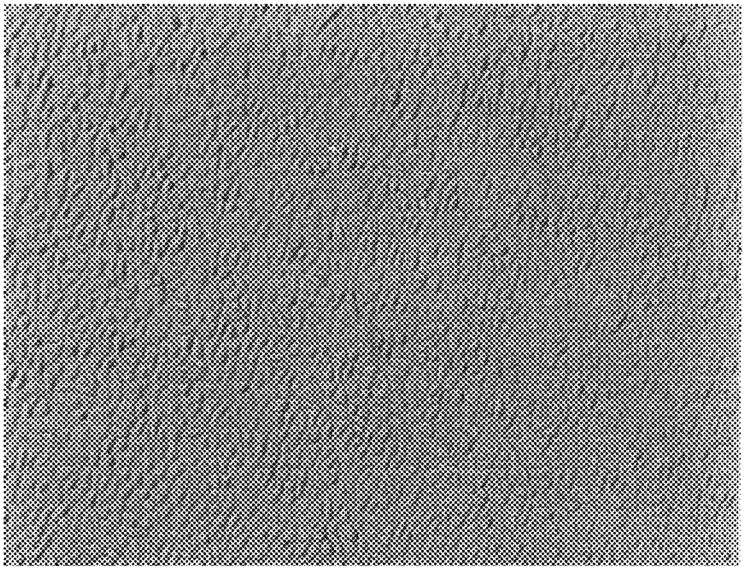
Figure 2B:
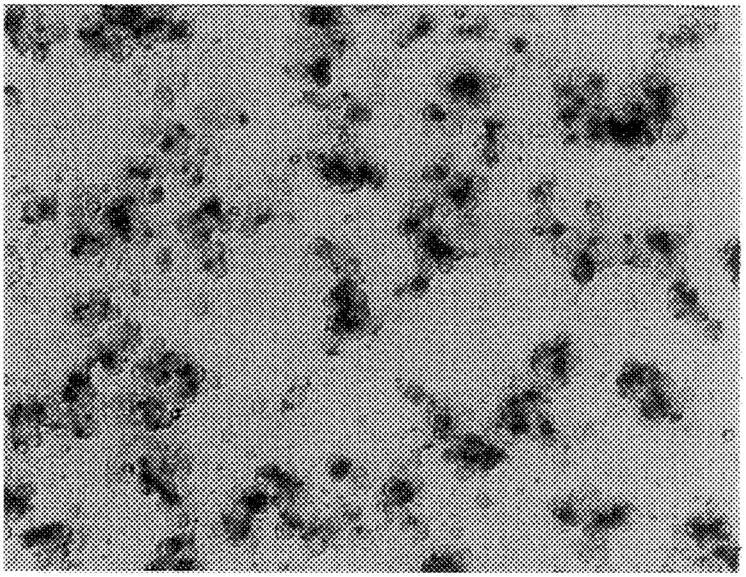
Figure 2C:
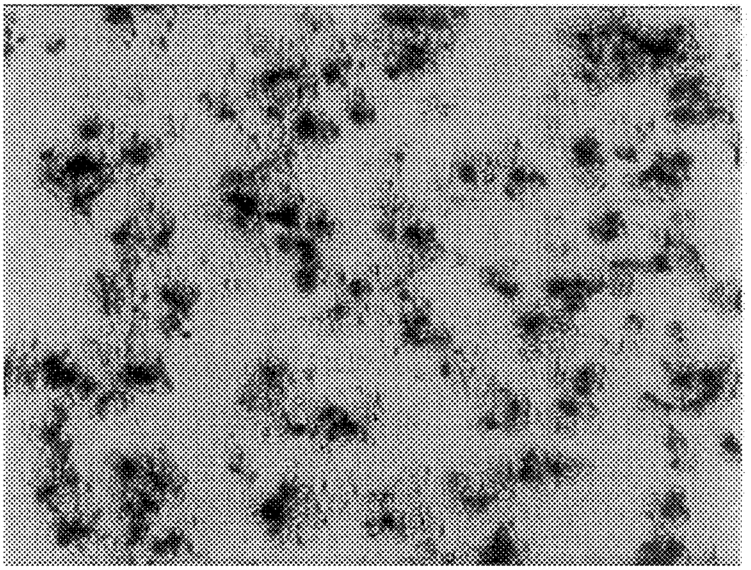

FIG. 2(A–C) shows cells infected with either AmEPV ATI-lacZ or spheroidin-lacZ recombinants at an m.o.i. of 10 PFU/cell. At 2 hr post infection, virus was removed, and the cells were co-infected with wild-type vaccinia virus. After 24 hours of vaccinia infection, the infected cells were stained with X-gal. Panel A, mock-infected cells; Panel B, AmEPV ATI-lacZ with vaccinia co-infected cells; and Panel C, AmEPV spheroidin-lacZ with vaccinia co-infected cells.

Figure 3:
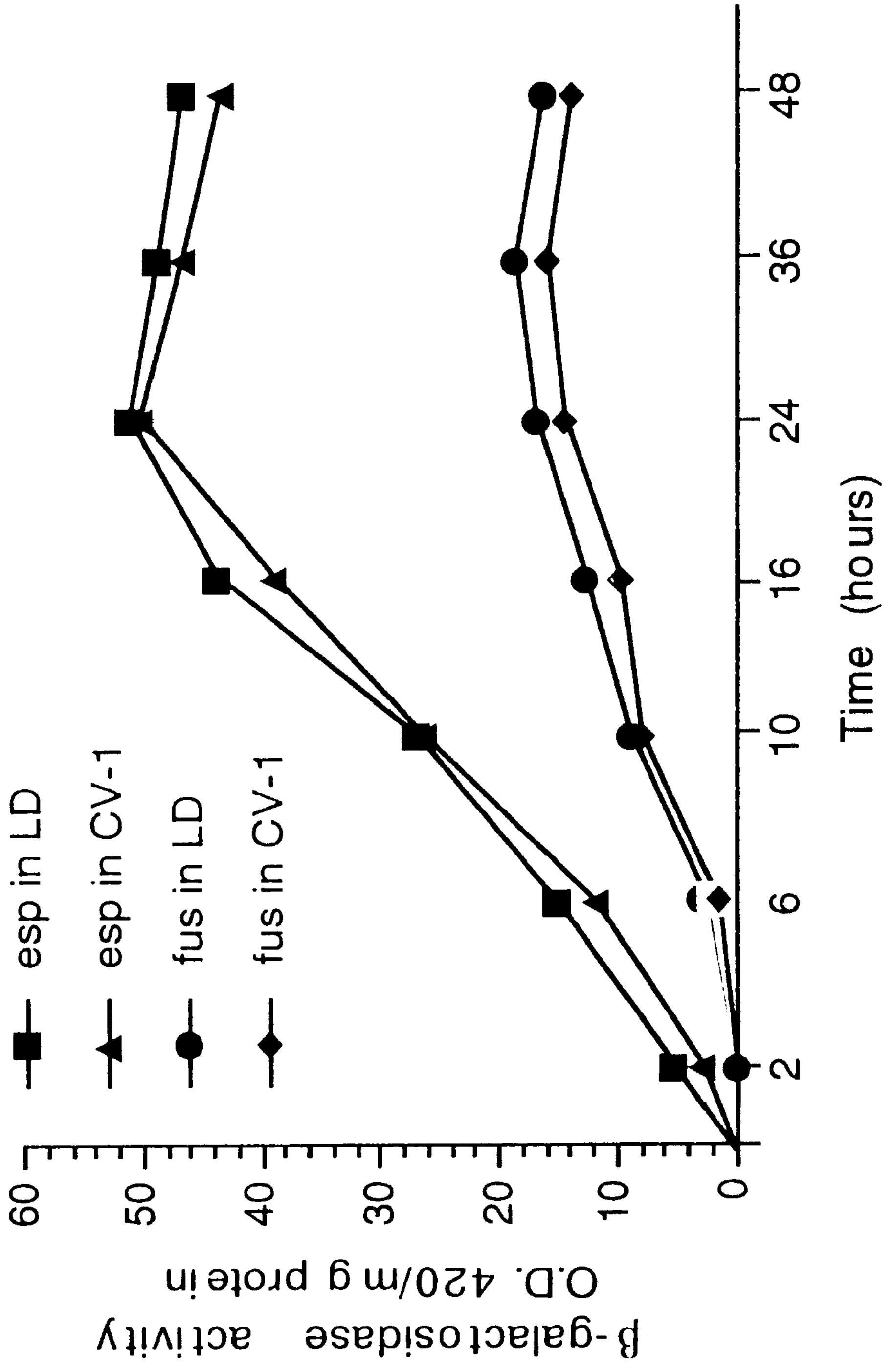

FIG. 3 shows a time-course of rEPV-mediated lacZ expression in CV-1 and LD-652 cells infected with rEPV fus-lacZ and esp-lacZ at an m.o.i. of 10 PFU/cell. After 2 hours of incubation, virus was removed and replaced with fresh medium. Infected cells were harvested at the indicated time points and extracts were prepared for beta-galactosidase activity assay. Each time point is the average of three independent assays. The levels of enzyme are fairly constant for about four days, indicating that the rEPV infected cells remain intact after infection, as opposed to typical poxviral infections of vertebrate cells, which generally result in cytolysis.

Figure 4:
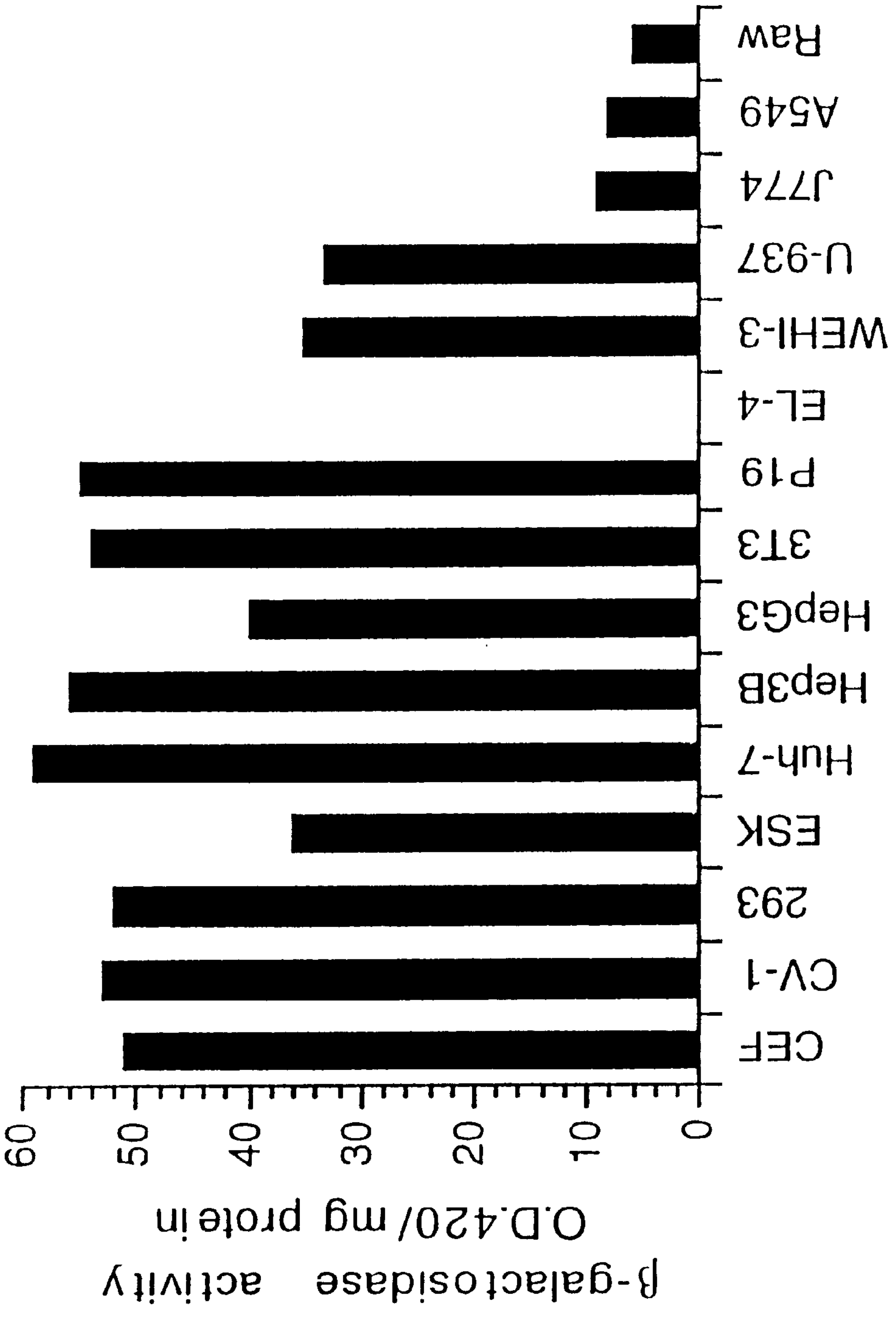

FIG. 4 is a histographic representation of beta-galactosidase expression in rEPV (esp-lacZ) infected vertebrate cell lines. Standard conditions for infections were: $4\times10^5$ cells/well in a 12-well plate, seeded 1 day prior to infection, and infected with rEPV at an m.o.i. of 10 PFU/cell. Cells were exposed to virus for 2 hours, the virus-containing medium removed, the cells washed with PBS, and fresh medium added. At 24 hours post-infection, beta-galactosidase activity assays were performed. Cells tested included: CEF, primary chicken embryo fibroblast cells; CV-1, African green monkey kidney epithelial cells; 293, human kidney; ESK, pig kidney; Huh-7, human hepatocarcinoma cells; Hep3B, human hepatocarcinoma cells; Hep G2, human hepatocarcinoma cells; EL 4, mouse lymphoma; WEHI-3, mouse myelomonocyte; U-937, human histiocytic lymphoma; J774, mouse monocyte macrophage; A549, human lung carcinoma; and RAW, mouse monocyte macrophage. As can be seen, beta-galactosidase expression was detectible in all cell types aside from the mouse lymphoma cells.

Figure 5:
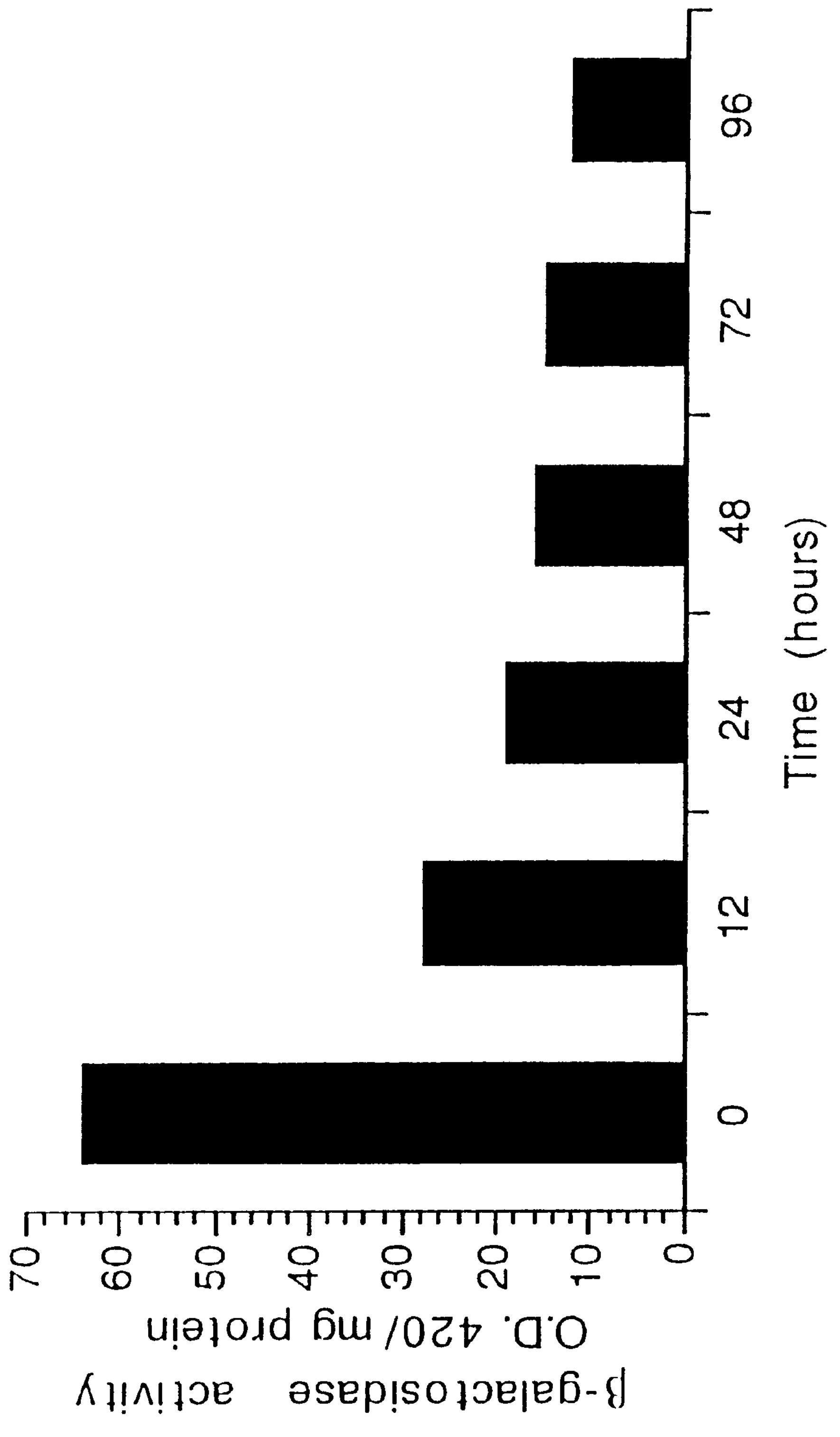
Figure 6A:
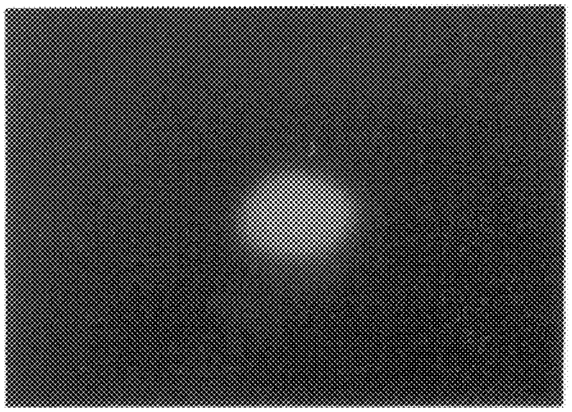
Figure 6B:
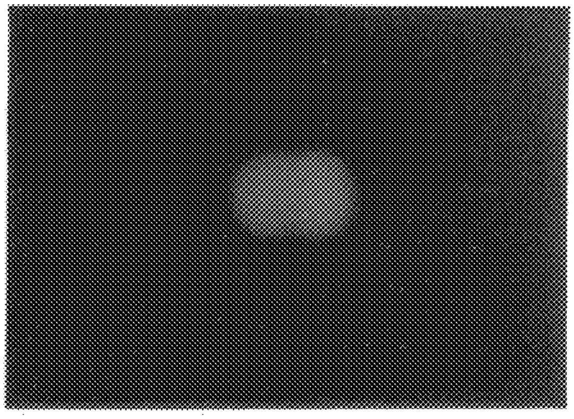
Figure 6C:
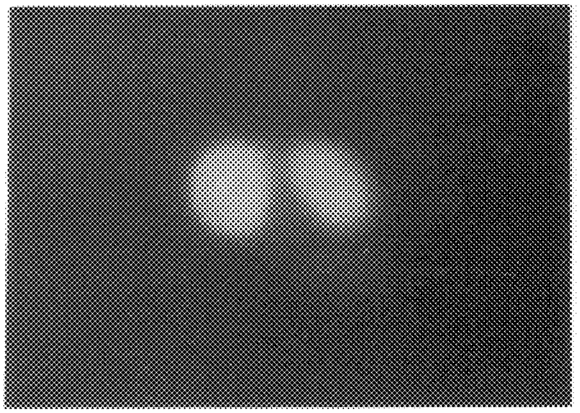
Figure 6D:
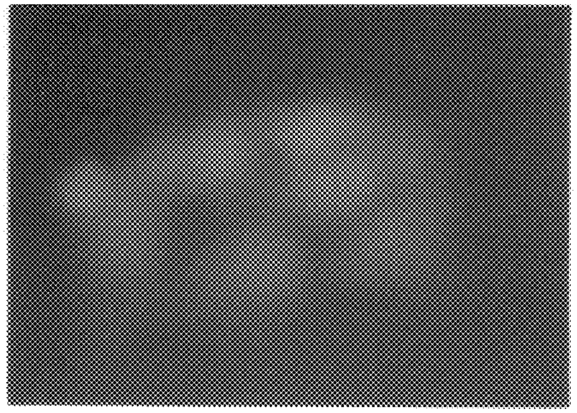

FIG. 5 demonstrates the persistence of rEPV after entry into mammalian cells. CV-1 cells were infected with rAmEPV ATI-lacZ at a m.o.i. of 10 PFU/cell. At 2 hours post infection, virus was removed and fresh medium added. After 0, 12, 24, 48, 72 and 96 hours of incubation, the medium was removed and the cells were co-infected with wild-type vaccinia virus. After 24 hours of vaccinia infection, cells were harvested and beta-galactosidase activity assays were performed. Each point is the average of three independent assays.

FIG. 6(A–D) demonstrates the survival of vertebrate cells after infection with rEPV. CV-1 cells were infected with rAmEPV esp-gfp at an m.o.i. of 1 PFU/cell. The individual fluorescent cells were located and followed over a period of 2 to 3 days and photographed using a fluorescence microscope. One fluorescent cell (Panel A) divided into two, (Panels B and C) and then more than six cells (Panel D).

Detailed Description of the Invention

This invention comprises preparation of a recombinant entomopoxvirus, (rEPV), such as the prototypical *Amsacta moorei* entomopoxvirus (AmEPV), by insertion of a gene encoding a heterologous protein into the EPV genome. This is accomplished via standard techniques of molecular biology known in the art. However, what is critical to the success of this invention is that the heterologous gene be placed under transcriptional control of an EPV or vertebrate poxvirus early gene promoter, or, upon translocation of the rEPV DNA to the nucleus, another promoter recognized by vertebrate cellular transcription factors. Thus, for example, a synthetic EPV early gene promoter may be used. Alternatively, the gene promoter of the EPV 42 kilodalton early gene product may be used. For this purpose, the disclosure of U.S. Pat. No. 5,174,993, and of Tine et al., 1996, which discloses the cloning and sequence of that promoter, are herein incorporated by reference. It is predictable, based on the instant disclosure, that any early EPV gene promoter could be used for this purpose, thereby affording variations in the strength of gene expression.

The molecular biology of the EPVs, unlike that of either the orthopoxviruses or baculoviruses, remains relatively unknown. However, over the past few years, we have standardized insect culture systems for study and growth of AMEPV, developed "shuttle plasmids" and constructed specialized (e.g. thymidine kinase negative) cell lines so that ready genetic manipulation of AmEPV is now possible (Gruidl et al., 1992; Hall et al., 1996; Hall et al., 1993; Moyer, 1994; Winter et al., 1995). These disclosures of standard methods are herein incorporated by reference.

AmEPV, like other poxviruses (e.g. vaccinia) is a cytoplasmic DNA virus, and the growth strategy in cell culture is quite similar for the two viruses. Because AmEPV is a cytoplasmic virus, a key feature of the infection cycle is that upon entry into insect cells, early viral genes are transcribed by enzymes derived from the previously infected cell that are packaged within the virion core. Following early gene expression in insect cells, viral DNA replication ensues, leading to formation of electron-dense cytoplasmic viral DNA-containing virosomes or "factories" followed by intermediate and late viral gene expression. Virion assembly then ensues, with concomitant packaging of the early transcription apparatus necessary to initiate the next round of infection. Spheroidin, the major constituent of AMEPV viral occlusion bodies, is the most highly expressed late AmEPV protein, ultimately constituting 40% of the total infected insect cell protein. Cowpox virus, a virus of vertebrates, contains an analogous A-type inclusion body (ATI) late protein, which is also highly expressed. However, the spheroidin promoter is not recognized in vaccinia recombinants containing the spheroidin gene, and under these conditions, spheroidin is not expressed (Hall et al., 1996), indicating that at least some AmEPV late promoters are specific for the insect cell environment.

Although AMEPV grows well in insect cells, infection of vertebrate cells is non-permissive. In FIG. 1, we demonstrate what occurs when vertebrate cells are infected with a series of AmEPV-lacZ recombinants. The foreign gene is preferably inserted within a non-essential gene, such as the thymidine kinase (TK) gene, of AmEPV or other entomopoxviruses. We discovered that when lacZ is driven by a late promoter, (either the ATI promoter (panel B) or spheroidin promoter (panel C), no expression of β-gal is observed. However, when lacZ expression is driven by either of the two early AmEPV promoters, one derived from the fusolin, fus, gene, one derived from the EPV of *Melolontha melolontha,* (AmEPV has no fusolin gene, see Gauthier et al., 1995), and the other from a gene encoding a 42k early AmEPV protein, high levels of β-gal were observed in the recombinant AmEPV infected vertebrate cells (panel D and panel E respectively). Furthermore, we reproduced this result in human liver cells infected with recombinant AmEPV wherein expression of the lacZ reporter gene was controlled by the EPV esp promoter (FIG. 1, panel F). These results provide clear evidence of AmEPV entry into vertebrate cells followed by early, but not late viral gene expression. We also noted that if cells infected with either of the rEPV recombinants used in FIG. 1, panels B & C are co-infected with vaccinia, β-gal expression from the rEPV wherein the lacZ was under control of a late promoter (ATIlacZ or sphlacZ) occurs, indicating that, under the proper circumstances, i.e. upon provision of the necessary transcriptional factors in trans, promoters other than early EPV promoters may be used to drive heterologous gene expression from rEPV infected vertebrate cells. Accordingly, in one embodiment of the present invention, the rEPV encodes an heterologous gene under the control of a promoter which is only active upon provision of required factors in trans. Such a rEPV could be induced to express the heterologous gene, for example, by co-infection with a replication deficient vaccinia virus. Alternatively, the rEPV particles could be produced in cells that are co-infected with vaccinia virus (see FIGS. 2 and 5 ). In yet a further alternative, the rEPV particles could be engineered to contain the necessary factors, for example, by routine experiments in which vaccinia virus is fractionated and the appropriate factors that lead to efficient rEPV expression driven by late genes added to the rEPV infection composition or viral particles.

The fact that EPV infections are abortive in vertebrate cells highlights fundamental differences between the vertebrate and insect poxviruses relevant to the issue of safety in using these viruses as vectors in humans or other vertebrates. However, like orthopoxviruses, there appears to be no obvious difference in infectivity when vertebrate cells are either growing or quiescent.

It is also important to note that we see no cytopathic effect of rEPV infection of vertebrate cells and believe that the vertebrate cells survive infection by rEPV, highlighting another unique feature of rEPV infections of vertebrate cells. Langridge (1983) indicated that vertebrate cells survive contact with EPV, but there was no disclosure or suggestion that rEPV could be used to deliver and express heterologous genes in vertebrates.

As noted above, we have confirmed the foregoing conclusions with AmEPV recombinants which contain the humanized *Aequorea victoria* green fluorescent protein (gfp) regulated by the 42k EPV or fusolin promoter (see FIG. 6). Upon infection, single, fluorescent cells are initially observed which proceed to divide, ultimately forming small clusters of fluorescent cells. These results provide definitive evidence that vertebrate cells survive rEPV infection.

As with other poxviruses, our experience has been that very large amounts of foreign DNA may be cloned into rEPV, another very useful feature of this virus. Therefore, according to this invention, rEPV enters vertebrate cells, to produce a non-permissive infection, early viral genes are expressed, and the infected cells survive and continue to divide. These properties, plus a very large capacity of the virus for foreign genes, are features which make recombinant EPVs excellent vectors for delivery of genes for transient gene expression in vertebrates.

In addition, we found that the level of expression in vitro in vertebrate cells is clearly detectable. Furthermore, there was little difference between the level of β-galactosidase detectable at day 1 post-infection and day 5 post-infection. This may be because the β-galactosidase produced is particularly resistant to degradation, or because the virus continues to express the enzyme and thereby replenishes enzyme that is degraded, (i.e. the virus is rather hardy and does not itself disintegrate very rapidly, continuing to express the foreign gene over several days). However, because the virus cannot get through its full genetic program in a vertebrate milieu, by definition, the expression is transient. Ultimately, the non-replicating virus disintegrates. In certain contexts, for example in acute respiratory distress syndrome, there is a transient massive inflammatory response in the lungs during or after surgery. In such a situation, prophylactic administration of a rEPV construct which transiently expresses an anti-inflammatory cytokine or a soluble cytokine receptor (such as a soluble TNF receptor which could then bind the excess available TNF that is suspected to be one of the causes of this condition) is precisely the type of medical intervention that is desirable.

The level of heterologous gene expression from EPV recombinants in vertebrate cells may also be enhanced by a number of techniques known in the art. For example, high-level expression from rEPV vectors is demonstrated by insertion of an inducible bacteriophage T7/lacZ or like expression cassette into the EPV genome. According to this embodiment of the invention, endogenous early AmEPV promoters are replaced by optimized promoters that operate within the EPV context. One method to achieve high levels of foreign gene expression includes use of the bacteriophage T7 promoter dependent expression system which has been adapted to vaccinia virus (Fuerst et al., 1986). Until recently, this system depended on the infection of individual cells with two separate recombinant vaccinia viruses, which is impractical in in vivo situations. The first virus contained the recombinant gene of choice under control of the T7 late promoter. The second virus contained the T7 RNA polymerase under control of an early vaccinia virus promoter. While in theory both the T7 RNA polymerase and foreign gene could be contained in a single virus, in practice these single virus constructs were frequently lethal due to leakage, which arrested viral replication. Recently, however, with the incorporation of additional regulatory signals and a temperature sensitive *E. coli* lac repressor, more stringent control over unintended expression has been achieved, giving 10,000 to 20,000 fold induction by a simple increase in temperature from a single virus vector which is induced only at high temperature (Alexander et al., 1992; Ward et al., 1995, herein incorporated by reference). According to these methods, in one embodiment of this invention, a recombinant EPV is produced which contains this inducible expression system. In this embodiment, for example, an early entomopoxvirus promoter is used to drive expression of the T7 polymerase gene product, and an heterologous gene under control of the T7 promoter is then expressed from the entomopoxvirus. The value of this two step expression system, known to be effective in other systems but not previously demonstrated in entomopoxvirus, is that substantial amplification of the expression event is thereby achieved. The rEPV desirably encodes a temperature sensitive or chemical sensitive repressor protein which is inactivated upon a temperature shift or upon provision of the de-repressive chemical. As disclosed by Ward et al., (1995), and in view of the instant disclosure, a "VOTE" expression system (vaccinia virus/lac operon/T7 RNA polymerase/EMC) could be adapted to the rEPV milieu by replacement of the vaccinia virus portion of the system with an appropriately engineered rEPV. Recently, Wu et al., (1997) reported that the inducible lactose operator-repressor system is functional in whole animals. That disclosure is hereby incorporated by reference for this purpose.

One inherent advantage of using EPV is that the normal growth temperature of the virus in insect cells is 26–28° C., well below the temperature (30° C.) at which the thermolabile elements of the T7/lacZ system are completely repressed. Accordingly, this form of the recombinant EPV vector eliminates any problems with levels of expression or leaky expression of the foreign gene of interest.

In a further embodiment of this invention, recombinant EPVs are used to deliver genes for stable integration into the vertebrate genome. This is achieved because, subsequent to non-permissive infection of vertebrate cells with recombinant entomopoxvirus, the EPV particles are degraded, releasing the viral DNA. A portion of that DNA may enter the nucleus, particularly when an appropriate nuclear localization signal is included in the rEPV, and integrate into the chromosomal DNA. Cells containing stable insertions are produced by infection with EPV recombinants containing a selectable marker, (for example, ecogpt [mycophenolic acid resistance] or neo [G418 resistance]), under control of the cytomegalovirus, CMV, early promoter, or like promoter known to be recognized by the vertebrate cellular machinery, to select for vertebrate cells permanently transformed following recombinant EPV infection. The frequency of obtaining such recombinants, and the site-directed nature of such integration, is increased by including sequences in the EPV recombinants which are homologous to the desired site of chromosomal integration. In addition, expression of genes under the control of vertebrate promoters in rEPV is enhanced by inclusion of any of a number of different nuclear localization signals into the rEPV (Nigg et al., 1985; Schmitz et al., 1991; Silver, 1991; each of which are herein incorporated by reference for this purpose). Thus, according to this embodiment of the invention, based on this disclosure and using such techniques as are known in the art, recombinant EPV may be used for the stable delivery of foreign genes into vertebrate cells.

In a further embodiment of this invention, in situ expression of foreign genes is accomplished by introduction of EPV recombinant vectors, for example, into the vertebrate lung. Reporter or biologically significant gene expression is achieved by use of lacZ and gfp recombinants of AmEPV driven by the 42k promoter or like promoter recognized by the EPV particle transcriptional factors. Virus is introduced via inhalation or intranasally into the lungs following known protocols (Martinez-Pomares et al., 1995; Thompson et al., 1993). Alternatively, lungs are inoculated using a fiberoptic bronchoscope (Flotte et al., 1993). In experimental animals, localized β-galactosidase expression according to these protocols is detected by harvesting the lungs 24 and 48 hours after administration of virus. The lungs are glutaraldehyde fixed, sectioned and stained with anti-p-galactosidase, horse-raddish peroxidase conjugate. gfp expression is demonstrated by fluorescence microscopy of lung tissue, fluorescence-activated cell (FACS) sorting of isolated cells or, in the case of rabbits, by direct fluorescence bronchoscopy.

The recombinant vector of this invention may be used in any of a number of contexts in which heterologous gene expression in vitro or in vivo is required. One such context is acute lung injury, clinically known as adult respiratory distress syndrome (ARDS), which is a major complication associated with several life-threatening illnesses. Gene therapy offers the possibility of altering the localized pulmonary environment through delivery and localized expression of selected proteins to prophylactically prevent or reduce susceptibility of lung cells to injury. In addition to such proteins as alpha-1-antitrypsin, or an anti-oxidant protein such as manganese superoxide dismutase, (Brigham et al., 1994, and 1995) there are as well a variety of viral encoded proteins which, in the context of a viral infection, serve to circumvent host inflammatory and immune responses. Herpes-, adeno- and poxviruses each encode such proteins (McFadden, 1995). These viral proteins include secreted soluble receptors/binding proteins/antagonists for cytokines and chemokines, as well as inhibitors of cysteine aspartic proteases, caspases (serpins). Currently, for the lung, liposomes, retroviruses, adenovirus and adeno-associated virus (AAV) have received the most attention as vectors to deliver such genes. This invention provides recombinant entomopoxviruses encoding the relevant heterologous gene product for the delivery and transient expression of genes of therapeutic importance, including those mentioned above for ARDS and other conditions.

In studies with adenovirus, in particular, inflammation and immunogenicity of the virus and virus-infected cells has limited transgene expression and the utility of this approach to treat chronic illnesses. Inflammation is initially characterized by perivascular and peribronchiolar inflammatory cell infiltration. Neutrophils and, later, macrophages and lymphocytes frequent the infected area. Specific cytokines can also be measured as an index of the inflammatory response (Ginsberg et al., 1991 Noah et al., 1996). Based on non-specific inflammatory responses delineated in lungs following infection with adenoviruses, the early response to adenovirus infections consist of diffuse cellular infiltration of peribronchiolar and alveolar regions associated with the appearance of several classes of pro-inflammatory cytokines (Ginsberg et al., 1991; Noah et al., 1996). These include TNFα, and IL-1, IL-6 AND IL-8 (KC/GRO in the mouse). There is considerable experimental evidence from rodents demonstrating that these classes of cytokines, and in particular TNFα and IL-8 (or KC/GRO), play central roles in the recruitment and activation of inflammatory cell populations in the lung. Based on the non-permissive infection of vertebrate cells by recombinant EPVs, it is expected that these adverse reactions will be much reduced compared to those observed with other gene transfer vectors known in the art. In addition, since vertebrate poxviruses are a rich source of anti-inflammatory proteins, including secreted IFN-γ, TNF,IL-1, serpins (McFadden, 1995) and chemokine receptors, any observed inflammatory response initiated by the recombinant EPV is controlled by cloning one or more of these genes into the EPV recombinant vector.

While not all vertebrate cells may be readily permissive to entomopoxvirus penetration, (hepatic cells seem to be particularly susceptible while lymphocytes appear to be rather resistant to infection by rEPV), it is predictable based on the positive results disclosed herein that optimization and routine modification of the infection procedures disclosed herein will lead to efficient rEPV infection and heterologous gene expression in most vertebrate cell and organ types, including in lymphocytes.

A variety of early entomopoxvirus and synthetic promoters fashioned, for example, after an early vaccinia virus promoter, are effective in driving expression in vertebrate cells infected with the recombinant entomopoxvirus. The synthetic early vaccinia virus promoter and several other like promoters are expected to be active. The specific invention contemplated requires that the promoter be or behave like an early EPV promoter. A gene promoter, for purposes of this invention, is considered to be an early EPV gene promoter if, within the context of an EPV in an insect host, the promoter is capable of driving expression of early entomopoxvirus genes.

The biochemistry of the entomopoxvirus contributes to its safety as a gene delivery vehicle in vertebrate systems, because the virus appears to be incapable of replication in the vertebrate host. Accordingly, large quantities of the recombinant virus are grown up in insect cells, where all of the promoters are active, and the thus produced virus is then used to infect vertebrate cells where the virus cannot replicate. As a result, these vectors provide significant safety advantages, whether they are used to deliver genes or to express an antigenic gene product to raise an immune response in vivo.

Typically, the recombinant EPV is delivered to vertebrate cells in vitro at a multiplicity of infection of 0.1 to 100, and preferably 1 to 10 PFU per cell. In vivo, the recombinant EPV of this invention is delivered at between about 0.01 $\mu$g/kg to 1 mg/kg, and preferably between about 0.1 $\mu$mg/kg to 10 $\mu$/kg. Those skilled in the art will appreciate that these dosages may need to be optimized, depending on the amount of heterologous gene sought to be delivered and the efficiency of cellular infection observed with a given recombinant EPV construct. In addition, where an immune response to an antigen encoded by the rEPV is desired, it will be recognized that increased dosages of the rEPV may be required to achieve a sufficiently high level of gene expression to achieve the desired cellular or humoral immune responses. It is predictable, based on the instant disclosure of rEPV mediated heterologous gene expression in vertebrate cells, and examples of such successes with different non-replicating vaccine systems known in the art (see for example Fleury et al., 1996, in which a recombinant canarypox expressing gp160 of HIV-1 followed by booster with recombinant gp160 was able to induce memory cytotoxic T lymphocytic responses in HIV-1 negative volunteers immunized with the recombinant virus) that a successful vaccine based on such recombinants may be produced for use in vertebrates, including humans.

Having generally described the various features of this invention, several specific examples are provided below to further describe this invention. However, it should be recognized that the scope of this invention is not to be measured by the specifics of these examples, but rather by the claims which are appended hereto.

EXAMPLE 1

Viruses and Cell Culture

AmEPV (Hall and Moyer, 1991) was replicated in IPLB-LD-652 cells (Goodwin et al., 1990) which were maintained at 28° C. in a 50:50 mixture of EX-CELL 401 media (EX-CELL) (JRH Biosciences, Lenexa, Kans.) and TC-100 media (Gibco, Gaithersburg, Md.), supplemented with 10% fetal bovine serum (FBS), 50 U of penicillin/ml and 50 $\mu$g of streptomycin/ml. A TK negative cell line designated C11.3 was selected by a process of adaptation of TK(+) LD652 cells to increasing levels (10 $\mu$g/ml), every 5 weeks, of 5-bromo-2'deoxyuridine (BUdR) up to 100 $\mu$g/ml BUdR over a period of one year and thereafter maintained in TE medium containing BUdR (100 $\mu$g/ml). Vaccinia virus (VV) strain WR (Condit and Motyczka, 1981) and cowpox virus, Brighton red strain, were produced at 37° C. in CV-1 cells, as well as in RK-13 and BSC40 cells, cultured in Eagle's minimal essential media with Earle's salts supplemented with 5% FBS, 50 U of penicillin/ml, and 50 $\mu$g of streptomycin/ml. Rat TK(-) cells were maintained in MEM medium containing BUdR (100 $\mu$g/ml). Other vertebrate cell lines used were grown in the medium recommended by the authors or by the ATCC.

EXAMPLE 2

Plasmid Construction

Plasmid pRH7, 6.073 kilobase pairs (Kb), ATCC 68902, contains the AmEPV spheroidin cassette with 306 base pairs (bp), of upstream and 92 bp of downstream sequence (DNA from bp 2774 to 6183 of GenBank locus AAVSPHERE). The DNA was prepared by cloning a T4 DNA polymerase blunted HaeII-BspI 1286 bp fragment (of genomic AmEPV DNA) into SmaI cut pUC9.

Plasmid pDU20lacZ was used to build a spheroidin negative recombinant AmEPV which contained a lacZ open reading frame driven by the spheroidin promoter plus 20 bp of additional sequence downstream of the starting ATG. pDU20lacZ, was prepared as follows: Oligonucleotide primers, RM316 and RM315, were used in a polymerase chain reaction (PCR) with a spheroidin promoter-containing plasmid, pRH512 (Hall and Moyer, 1991), template. The PCR conditions were 30 cycles of 94° C. for 1 min, 45° C. for 1 min, 72° C. for 1 min, and subsequently 72° C. for 8 min complete the extensions. RM316 was from bp 2056 to 2075 of GenBank locus AAVSPHERE and had the sequence:

ACAGGAGCTCGCTATTATAACTAATGTGAG (SEQ. ID: 1). RM315 was from bp 3102 to 3083 of GenBank locus AAVSPHERE and had the sequence:

CACAGGATCCGTTGCTAAAGGTACGTTACT (SEQ.ID:2). Collectively, these two primers produced a 1046 bp fragment which had a 5' SacI site and a 3' BamHI site. This fragment contained 1023 bp of upstream spheroidin sequence, the starting ATG of the spheroidin gene sequence, and 20 bp of spheroidin coding sequence following the ATG start signal. In a separate PCR reaction, oligonucleotide primers, RM313 and RM314, were used to amplify a 998 bp fragment of spheroidin coding sequence using pRH7 as a template. RM313 was from bp 4357 to 4376 of GenBank locus AAVSPHERE and had the sequence:

AGAGAAGCTTCAGCCCAGATACTACGATTC (SEQ. ID:3). RM314 was from bp 5355 to 5336 of GenBank locus AAVSPHERE and had the sequence:

CACAGTTAACACACTTGATGCAACTCTAGC (SEQ. ID:4). This PCR-produced fragment contains a 5' HindIII and a 3' HincII site. These two PCR products were separately cloned into the SacI+-BamHI site and the HindII+-HincII site of pBluescript I SK(+) to produce an intermediate vector, pDU20 (5.0 Kb). PDU20 was cut with BamHI and a lacZ gene with BamHI ends (from plasmid pMC1871, Pharmacia Biotech, Piscataway, NJ) was inserted to produce pDU20lacZ.

Plasmid pTK-ATIlacZ was prepared using primers RM325 (ACAGGAGCTCGAATTCAAGTTAAATATTTA, SEQ.ID.:5) and RM326, (CACAGGATCCCTGGCAAAACAACAGAATTG, SEQ.ID. :6), bp 1–20 and bp 748–729, respectively, of GenBank locus AAVTHYKIN, to amplify a 748 bp fragment of downstream flanking sequence using plasmid pMEGTK-1 (Gruidl et al., 1992). This PCR product contains a 5' SacI and a 3' BamH1 site. Oligonucleotide primers RM327, (AGAGAAGCTTCAAAATGGATTTACTAAATTC, SEQ.ID.:7), and RM328, (CACAGTTAACGAATTCATATTCAATTATAT, SEQ.ID.:8), from bp 848 to 868 and 1511–1492, respectively, of GenBank locus AVVTHYKIN were used to amplify a 663 bp fragment of upstream flanking sequence using pMEGTK-1. This fragment contains a 5' HindIII and a 3' HincII site. These two fragments were separately inserted into the SacI-BamHI and HindIII and HincII sites of pBluescript I SK(+) to produce an intermediate plasmid pDUTK. A cowpox virus A type inclusion (ATI) promoter-driven lacZ gene cassette, which was from pATIlacZ plasmid (Hall et al., 1996) was digested with Kpnl, blunted with T4 DNA polymerase, and digested with PstI. This ATI promoter-driven lacZ gene cassette was inserted into the EcoRV and PstI site of pDUTK to produce pTK-ATIlacZ.

pTK-fus-lacZ: The *Melolontha melolontha* EPV early fusolin gene promoter was PCR-amplified using the following primers and the pHF51 plasmid (Gauthier et al. 1995) containing the whole fusolin gene as a template: RM504 (ACAGGATCCGTACGTATATTAATCATGATT, SEQ.ID.:9), RM505 (GACCCATGGTAAAGATCTTTGGTAATAATA, SEQ.ID.:10). This 275 bp fragment containing the 5' BamHI and 3' NcoI sites was digested by only BamHI and inserted into the BamHI and SmaI sites of pDUTK to produce the plasmid pTK-fus. The lacZ gene digested with PstI and SmaI from pMC1871 (Pharmacia Biotech, Inc., Piscataway, N.J.) was inserted into the pTKfus plasmid which was first digested with NcoI, blunted with T4 DNA polymerase, then digested with PstI to produce pTK-fus-lacZ (SEQ.ID.:11, which provides the entire sequence of pBluescript II KS(+) with the fus-lacZ insert; naturally, this insert may be replaced by any other desired insert).

pTK-esplacZ: One hundred and sixty nine additional base pairs of 5' AmEPV 42kDa protein gene promoter sequence beyond that presented by Paoletti, (1992), was derived by sequencing an appropriate SspI clone of AmEPV DNA, identified by use of a library prepared by ligating 3 to 4 kb fragments of partially SspI-digested AmEPV DNA into SmaI-cut pUC19, and hybridization screening of this library using a 42kDA-gene-promoter-specific PCR-produced probe amplified from a genomic AmEPV template with primers RM558 (TCAAAAAAATATAAATGATTCACC, SEQ.ID.:12), and RM520 (GACCCATGGCGATTTTATATTGTAATTATA, SEQ.ID.:13), both based upon the known sequence (Paoletti, 1992). A 285 bp fragment of the AmEPV early strong promoter (esp) was PCR-amplified using the following primers and appropriate AmEPV viral DNA as a template: RM519 (ACAAGATCTATAATAATGTAAAATCGCAGT, SEQ.ID.: 14) and RM520 (SEQ.ID.:13:). This fragment, containing 5' BglII and 3' NcoI sites was digested with NcoI and inserted into the SnaB1and NcoI sites of pTK-fus-lacZ to produce pTK-esp-lacZ (SEQ.ID.: 15:, which provides the entire sequence of pBluescript II KS(+) with the esp-lacZ insert; naturally, this insert may be replaced by any other desired insert).

pTK-esp-gfp: A green fluorescent protein (gfp) gene was PCR-amplified using the following primers starting with pTR-UF5 plasmid DNA (from Vector Core, University of Florida, Zolotukhin et al., 1996) as a template: RM 547 AGTCTCATGAGCAAGGGCGAGGAAC, SEQ.ID.: 16) and RM 548 (ACCCAAGCTTCCGCGGCCGCTCACTTGTAC, SEQ.ID.:17:). This 285 bp fragment containing 5' BspHI and 3' HindIII sites was inserted into NcoI (NcoI is compatible with BspH1) and HindIII sites of pTK-esp-lacZ. Thus, the lacZ gene of pTK-esp-lacZ was replaced with the gfp gene to produce pTK-esp-gfp.

EXAMPLE 3

Preparation of the AmEPV vector

LD-652 insect cells in a well of a 6-well plate were infected with wild-type AmEPV at a multiplicity of infection (m.o.i.) of five PFU per cell in a volume of 1 ml. Two hours post-infection (p.i.), the inoculum was aspirated and 1 ml of the diluted transfection mix was added. The concentrated transfection mix was prepared by separately combining 20 $\mu$l Lipofectin (Gibco, Gaithersburg, Md.) and 80 $\mu$l of a 50:50 mix of EX-CELL and TC-100 media without FBS (50:50 media), and 5 $\mu$g of pDU20lacZ plasmid in a volume of 100 $\mu$l of the same media. This was allowed to complex at room temperature for 15 min. This concentrated transfection mix was diluted by adding 800 $\mu$l of the 50:50 media without FBS. After six hours, the transfection mix was removed and replaced with 2 ml of 50:50 media with 10% FBS. The infection was continued for three days and the supernatant harvested by centrifugation at 200×g. Dilutions at $10^{-2}$ to $10^{-4}$ of the supernatant were made and used to infect cells in 6-well plates. After two hours, the supernatant was aspirated. The cells were overlaid with 2 ml of 1% SeaPlaque agarose prepared in TC-100 media supplemented with 10% FBS, equilibrated to 40° C., to which X-gal had been added to a final concentration of 120 $\mu$g/ml. The 1% agarose overlay was prepared by combining appropriate amounts of autoclaved, 40° C. equilibrated, 4% agarose, prepared in water, and 40C equilibrated 1.33×TC-100 media. A 1.33×solution of TC-100 media was prepared by using powered media, adjusting to pH6.2 with a 5 M potassium hydroxide solution, and sterile filtering. Plates were examined for blue plaques after four or five days. Plaques were picked with a Pasteur pipette and placed in 1 ml of TC-100 media plus 10% FBS and stored overnight at 4° C. The tube was vortexed and dilutions of $10^{1}$ to $10^{-3}$ were made. Plaques were purified four times. Recombinant virus was stored at 4° C. for two or three months or at −70° C. for long-term storage.

Preparation of rEPV encoding any other heterologous gene (other than lacZ) are prepared using a similar strategy and an appropriately constructed plasmid vector such as those defined in Example 2 above. By this means, we prepared a rEPV encoding the fluorescent protein gfp, which allowed us to demonstrate that vertebrate cells infected with rEPV and expressing an heterologous gene do not die, unless a gene product is intentionally chosen which leads to cell death. Accordingly, it is predictable based on these results that any heterologous gene could be inserted into a non-essential EPV gene and used to infect vertebrate cells. Thus, the gene chosen may encode an anti-inflammatory protein, an antigen, a cytokine, a receptor, an anti-sense sequence, or a structural protein. Insertions into the EPV spheroidin gene are achieved according to methods known in the art (Hall et al., 1996). Other sites of insertion are also known in the art (Dall, WO 93/25666).

Selection of TK(−) recombinants, where heterologous genes are inserted into the EPV TK gene, was facilitated by use of C11.3 TK(−) cells, which are derivatives of the LD-652 cells as described above.

Upon production of the desired rEPV in insect cells, the insect cells are destroyed by the virus. Extracellular virus was concentrated by centrifugation (20,000 rpm; 2 hours in an SW28 rotor). The viral pellet was resuspended in PBS. Virus titer was estimated by plaque assay on LD-652 insect cells according to methods known in the art.

EXAMPLE 4

β-galactosidase in-situ staining

In order to visualize the cells which were expressing lacZ, a histochemical stain for β-galactosidase (Sanes et al., 1986) was used. For the in situ assay, infected cells were rinsed on the plate with phosphate buffered saline solution (PBS; 150 mM sodium chloride, 15 mM sodium phosphate, pH 7.3) and fixed for 5 min by overlaying with a solution of 2% formaldehyde plus 0.2% glutaraldehyde prepared in PBS. This was aspirated and the cells rinsed with PBS and overlaid with a reaction mixture which consisted of 1 mg/ml X-gal (5-bromo-4-chloro-3-indolyl-β-D-galactosidase), 5 mM potassium ferricyanide, 5 mM potassium ferrocyanide, and 2 mM magnesium chloride prepared in PBS. The stock X-gal was 40 mg/ml prepared in dimethylsulfoxide. The cells were overlaid for 14 to 18 hrs at 37° C. to allow color development. The cells were rinsed with PBS and overlaid with a solution of 45% glycerol. Cells in which the lacZ gene is expressed show a blue to black color.

Alternatively, IPLB-LD-652 cells ($2\times10^5$ cells/well) or CV-1 cells ($4\times10^5$ cells/well) in 12-well plates were infected with rEPV at a m.o.i. of about 10 PFU/cell for 2 hours, after which the inoculum was aspirated, the cells rinsed with serum-free TE medium or MEM medium, 1 ml of fresh medium added to each well, and at appropriate times post-infection, the infected cells were harvested by scraping and freezing at −70° C. until assayed. The β-gal activity was performed using O-nitrophenyl-β-D-galactopyranoside (ONPG) as the substrate (Miller, 1972). β-gal activity was measured at 420 nm and normalized as the optical density (420 nm) per milligram of total protein.

EXAMPLE 5

Expression of Reporter Genes in Vertebrate Cells from a Recombinant AmEPV Containing an Early EPV Gene Promoter AmEPV recombinants with the lacZ gene under the control of either late (ATI promoter or the EPV spheroidin promoter) or early (AmEPV esp promoter of MmEPV fusolin) promoters. The AmEPV recombinants were then used to infect CV-1 cells. After 24 hours, the infected cells were stained with X-gal. With lacZ driven by a late promoter, either the ATI (FIG. 1B) or spheroidin (FIG. 1C) promoter, no β-gal expression or cytopathic effects were observed. However, when CV-1 cells infected with these recombinants were co-infected with vaccinia virus, β-gal expression from the rEPV ATIlacZ (FIG. 2B) and the sphlacZ (FIG. 2C) recombinants occured. This demonstrates that the rEPV successfully infected the vertebrate cells, but were unable, on their own, to express genes under control of late gene promoters. The co-infection with vaccinia virus apparently provides factors in trans which enables expression from these late gene promoters to occur. However, for the early gene promoters, co-infection with vaccinia was not required. This is apparently because entomopoxviruses, like vertebrate poxviruses, have all the necessary enzymatic factors and co-factors packaged in the viral particle for early gene expression to occur and upon which mid-to late-gene expression, and therefore replication, depends. Thus, early EPV gene expression is independent of viral replication and is also independent of vertebrate cell transcriptional factors (with expression largely occurring in the cytoplasm). LacZ expression driven by either of two early EPV promoters, fusolin (FIG. 1D) and esp (FIG. 1E) occurs at high levels in rEPV infected CV-1 cells and in human liver Huh-7 cells (FIG. IF). For these experiments, CV-1 cells were exposed to the fus-lacZ and esp-lacZ rEPVs for approximately 2 hours, after which the cells were harvested at various times and quantitatively assayed for β-gal activity as described above. As shown in FIG. 3, β-gal activity was detected as early as 2 hours post-infection for the esp-lacZ rEPV and 6 hours post-infection for the fus-lacZ, with expression peaking at about 12–24 hours post-infection, and then gradually declining. B-gal activity for both fus-lacZ and esp-lacZ in LD or in CV-1 cells remained almost unchanged for an extended period. The esp promoter appears to be about twice as strong of a promoter in both vertebrate cells and insect cells as the fusolin promoter.

EXAMPLE 6

Expression of Genes Under Control of EPV Late Gene Promoters Upon Co-Infection with Vaccinia Virus To demonstrate the ability of vaccinia virus to provide factors in trans which permit expression of genes under the control of a late EPV promoter, we set up two dishes of CV-1 cells. Both were infected with a recombinant AmEPV vector, (ATIlacZ or sphlacZ) at an m.o.i. of at least 5 PFU/cell, in MEM media. After 2 hr the inoculum was removed and the cells rinsed with PBS. To one of these dishes of infected cells, an inoculum of wild-type vaccinia virus at an m.o.i. of at least 5 PFU/cell was added. To the second dish of rEPV infected CV-1 cells, only medium was added. After 48 hr at 37° C., the cells in both plates were stained in situ to test for the presence of β-galactosidase. Blue CV-1 (β-galactosidase positive) cells were observed in the dish of cells which was co-infected with both vaccinia virus and AmEPV but not in the dish of cells which was inoculated with AmEPV alone. The CV-1 cells were not killed in the dish of cells inoculated with AmEPV only. This experiment shows that in the presence of vaccinia virus co-infection, the recombinant AmEPV vector was able to enter the vertebrate cells, to uncoat, and express the lacZ gene from a late AmEPV promoter (spheroidin) or the ATI promoter.

EXAMPLE 7

Susceptibility of Vertebrate Cell Lines to rEPV-Mediated Gene Transfer

The esp-lacZ rEPV was used to infect a variety of vertebrate cell lines and β-gal expression was examined by β-gal activity assay and X-gal staining of infected cells. Mock-infected and rEPV ATI-lacZ infected cells were used as controls. Of fifteen cell lines assayed, none from the mock or ATI-lacZ infected cells were positive for β-gal expression. Cells from liver, kidney, embryo were positive for β-gal expression when infected with the esp-lacZ rEPV, (see FIG. 4),with more than 30% of cells staining with X-gal 24 hours post-infection.

EXAMPLE 8

Persistence of rEPV Expression in Vertebrate Cells

A “rescue” experiment was conducted as follows: CV-1 cells were infected with rEPV ATI-lacZ at an m.o.i. of 10

PFU/cell for two hours. The inoculum was removed and fresh medium was added. After 0, 12, 24, 48, 72 and 96 hours post-infection, the cells were co-infected with vaccinia virus at an m.o.i. of about 10. Twenty-four hours post-vaccinia co-infection, β-gal activity was measured. Such activity was detectable even after four days post-rEPV infection, although at reduced levels (see FIG. 5).

EXAMPLE 9

Mammalian Cell Survival After Infection with rEPV

CV-1 cells infected with rEPV encoding esp-lacZ or fus-lacZ did not cause cell death or cytopathic effects (see FIG. 1). In addition, we were able to show that rEPV infected mammalian cells continue to grow and divide after such infection by infecting CV-1 cells with rEPV encoding the green fluorescent protein gfp under control of the EPV esp promoter. The CV-1 cells were infected at a low m.o.i. The individually infected cells were located by fluorescence microscopy, and then followed over the course of 2–3 days, during which single infected cells divided into two, then four and then more than six cells, with all daughter cells continuing to fluoresce, although diminishing in intensity with each round of cell division (see FIG. 6).

In view of the foregoing disclosure, the exemplary support provided herein and the sequences provided herewith, those skilled in the art will recognize and be able to produce rEPVs encoding any heterologous gene of interest, whether the gene encodes an antigen, enzyme, glycoprotein, receptor, cytokine, hormone, or anti-sense nucleic acid, for expression of the product encoded by the heterologous nucleic acid in vertebrate cells. The specifics of the foregoing disclosure should therefore not be construed as limiting to the scope of the claims which follow.

REFERENCES

Alexander, W. A., B. Moss, and T. R. Fuerst. 1992. Regulated expression of foreign genes in vaccinia virus under the control of bacteriophage T7 RNA polymerase and the *Escherichia coli* lac repressor. J. Virol. 66:2934–2942.

Arif, B. 1995. Recent advances in the molecular biology of entomopoxviruses. J. Gen. Virol. 76:1–13.

Boyce, F. M., and N. L. R. Bucher. 1996. Baculovirus-mediated gene transfer into mammalian cells. Proc. Natl. Acad. Sci. U.S.A 93:2348–2352.

Brigham, K. L. and A. E. Canonico, B. O. Meyrick, H. Schreier, A. A. Stecenko, and J. T. Conary. 1994. Gene therapy for inflammatory diseases. Prog. Clin. Biol. Res. 388:361–365.

Brigham, K. L. and A. A. Stecenko. 1995. Gene therapy in acute critical illness. New Horiz. 3:321–329.

Chalfie, M., Tu, Y., Euskirchen, G., Ward, W. W., and D. C. Prasher. 1994. Green fluorescent protein as a marker for gene expression. Science 263:802–805.

Condit, R. C., and A. Motyczka. 1981. Isolation and preliminary characterization of temperature-sensitive mutants of vaccinia virus. Virology 113:224–241.

Dall, Dec. 23, 1993, WO 93/25666, Recombinant Entomopoxviruses.

Fleury, B., Janvier, G., Pialoux, G., Buseyne, F., Robertson, M.N., Tartaglia, J; Paoletti, E., Kieny, M.P., Excler, J.L., and Y. Riviere. 1996. Memory cytotoxic T lymphocyte responses in human immunodeficiency virus type 1 (HIV_1)-negative volunteers immunized with a recombinant canarypox expressing gp 160 of HIV-1 and boosted with a recombinant gp160. J. Infect. Dis. 174(4):734–738.

Flotte, T. R., S. A. Afione, C. Conrad, S. A. McGrath, R. Solow, H. Oka, P. L. Zeitlin, W. B. Guggino, and B. J. Carter. 1993, Stable in vivo expression of the cystic fibrosis transmembrane conductance regulator with an adeno-associated virus vector. Proc. Natl. Acad. Sci. U.S.A. 90:10613–10617.

Fuerst, R. R., E. G. Niles, F. W. Studier, and B. Moss. 1986. Eukaryotic transient-expression system based on recombinant vaccinia virus that synthesizes bacteriophage T7 RNA polymerase. Proc. Natl. Acad. Sci. U.S.A. 83:8122–8126.

Gauthier, L., F. Cousserans, J. C. Veyrunes, and M. Bergoin. 1995. The *Melolontha melolontha* entomopoxvirus (MmEPV) fusolin is related to the fusolins of lepidopteran EPVs and to the 37K baculovirus glycoprotein. Virology 208:427–436.

Ginsberg, H. S., L. L. Moldawer, P. B. Sehgal, M. Redington, P. L. Kilian, R. M. Chanock, and G. A. Prince. 1991. A mouse model for investigating the molecular pathogenesis of adenovirus pneumonia. Proc. Natl . Acad. Sci. U.S.A. 88:1651–1655.

Granados, R. R. 1981. Entomopoxvirus infection in insects, p.101–126. In E. W. Davidson, ed., Pathogenesis of Invertebrate Microbial Diseases. Allanheld, Osmun & Co., Totowa, N.J.

Goodwin, R. H., Adams, J. R., and M. Shapiro. 1990. Replication of the entomopoxvirus from *Amsacta moorei* in serum-free cultures of a gypsy moth cell line. J. Invert. Pathol. 56:190–205.

Gruidl, M. E., R. L. Hall, and R. W. Moyer. 1992. Mapping and molecular characterization of a functional thymidine kinase from *Amsacta moorei* entomopoxvirus. Virology 186:507–516.

Hall, R. L., Y. Li, J. A. Feller, and R. W. Moyer. 1996. The *Amsacta moorei* entomopoxvirus spheroidin gene is improperly transcribed in vertebrate poxviruses. Virology 224:427–436.

Hall, R. L., and Moyer, R. W. 1991. Identification, cloning, and sequencing of a fragment of *Amsacta moorei* entomopoxvirus DNA containing the spheroidin gene and three vaccinia virus related open reading frames. J. Virol. 65:6516–6527.

Hall, R. L. and R. W. Moyer. 1993. Identification of an Amsacta spheroidin-like protein within the occlusion bodies of Choristoneura entomopoxviruses. Virology 192:179–187.

Holowczak, J. A. 1972. Uncoating of poxviruses. I. Detection and characterization of subviral particles in the uncoating process. Virology 50:216–232.

Hofman, C., Sandig, V., Jennings, G., Rudolph, M., and P. Schlag. 1995. Efficient gene transfer into human hepatocytes by baculovirus vectors. Proc. Natl. Acad. Sci. U.S.A. 92:10099–10103.

Langridge, W. H. 1983. Detection of *Amsacta moorei* entomopoxvirus and vaccinia virus proteins in cell cultures restrictive for poxvirus multiplication. J. Invertebr. Pathol. 42:77–82.

Martinez-Pomares, L., J. P. Thompson, and R. W. Moyer. 1995. Mapping and investigation of the role in pathogenesis of the major unique secreted 35-kDa protein of rabbitpox virus. Virology 206:591–600.

McFadden, G. 1995. Viroceptors, virokines and related immune modulators encoded by DNA viruses. R. G. Landes/Springer-Verlag, Austin, Tex.

Miller, J. H., Ed. 1972. Experiments in Molecular Genetics. p352–335. Cold Spring Harbor Laboratory, Cold Spring Harbor, N.Y.

Moyer, R. W. 1994. Entomopoxviruses, p. 393–397. In R. G. Webster and A. Granoff (eds.), Encyclopedia of Virology. Academic Press, Ltd., London.

Nigg, E. A., Hilz, H., Eppenberger, H. M., and F. Dutly. 1985. Rapid and reversible translocation of the catalytic subunit of cAMP-dependent protein kinase type II from the Golgi complex to the nucleus. EMBO J. 4:2801–2806.

Noah, T. L., I. A. Wortman, P. C. Hu, M. W. Leigh, and R. C. Boucher. 1996. Cytokine production by cultured human bronchial epithelial cells infected with a replication-deficient adenoviral gene transfer vector or wild-type adenovirus type 5. Am. J. Respir. Cell Mol. Biol. 14:417–424.

Palmer, C. P., Miller, D. P., Marlow, S. A., Wilson, L. E., Lawrie, A. M., and L. A. King. 1995. Genetic modification of an entomopoxvirus: deletion of the spheroidin gene does not affect virus replication in vitro. J. Gen. Virol. 76:15–23.

Paoletti, E. Dec. 29, 1992, U.S. Pat. No. 5,174,993.

Sanes, J. R., Rubenstein, J. L. R., and J-F. Nicolas. 1986. Use of a recombinant retrovirus to study post-implantation cell lineage in mouse embryos. The EMBO J. 5(12) :3133–3142.

Sarov, I., and W. K. Joklik. 1972. Characterization of intermediates in the uncoating of vaccinia virus DNA. Virology 50:593–602.

Schmitz, M. L., Henkel, T., and Baeuerle, P. A. 1991. Proteins controlling the nuclear uptake of NF-KB, Rel and dorsal. Trends Cell Biol. 1:130–137.

Silver, P. A. 1991. How proteins enter the nucleus. Cell 64:489–497.

Thompson, J. R., P. C. Turner, A. N. Ali, B. C. Crenshow, and R. W. Moyer. 1993. The effects of serpin gene mutations on the distinctive pathobiology of cowpox and rabbitpox virus following intranasal inoculation of Balb/c mice. Virology 197:328–338.

Tine, J. A., Lanar, D. E., Smith, D. M., Wellde, B. T., Schultheiss, P., Ware, L. A., Kauffman, E. B., Wirtz, R. A., De Taisne, C., Hui, G. S. N., Chang, S. P., Church, P., Hollingdale, M. R., Kaslow, D. C., Hoffman, S., Guito, K. P., Kallou, W. R., Sadoff, J. C. and E. Paoletti. 1996. NYVAC-Pf7: a poxvirus-vectored, multiantigen, multistage vaccine candidate for *Plasmodium falciparum* malaria. Infect. Immun. 64:3833–3844.

Ward, G. A., C. K. Stover, B. Moss, and T. R. Fuerst. 1995. Stringent chemical and thermal regulation of recombinant gene expression by vaccinia virus vectors in mammalian cells. Proc. Natl. Acad. Sci. U.S.A. 92:6773–6777.

Warren, J. S., K. R. Yabroff, D. G. Remick, S. L. Kunkel, S. W. Chensue, R. G. Kunkel, K. J. Johnson, and P. A. Ward. 1989. Tumor necrosis factor participates in the pathogenesis of acute immune complex alveolitis in the rat. J. Clin. Invest. 1873–1882.

Winter, J., R. L. Hall, and R. W. Moyer. 1995. The effect of inhibitors on the growth of the entomopoxvirus from *Amsacta moorei* in *Lymantria dispar* (gypsy moth) cells. Virology 211:462–473.

Wu, J. D., Hsueh, H. C., Huang, W. T., Liu, H. S., Leung, H. W. C., Ho, Y. R., Lin, M. T., and M. D. Lai. 1997. The inducible lactose operator-repressor system is functional in the whole animal. DNA Cell Biol. 16:17–22.

Yuen, K-C., and B. Arif., Aug. 16, 1994, U.S. Pat. No. 5,338,679.

Zaslavsky, V. 1985. Uncoating of vaccinia virus. J. Virol. 55:352–356.

Zolotukhin, S., Potter, M., Hauswirth, W. W., Guy, J., and N. Muzyczka. 1996. A "humanized" green fluorescent protein cDNA adapted for high level expression in mammalian cells. J. Virol. 70:4646–4654.

What is claimed:

1. A recombinant entomopoxvirus(rEPV) comprising an early entomopoxvirus gene promoter, an early vaccinia virus gene promoter or an early poxvirus promoter recognized by vertebrate transcriptional factors, wherein said promoter is operatively linked to a heterologous gene, and further comprising a nuclear localization signal directing translocation of said rEPV into a vertebrate cell nucleus.

2. The rEPV of claim 1 wherein said promoter is the EPV 42k gene promoter, the EPV fusolin gene promoter or a natural or synthetic vaccinia virus early gene promoter.

3. The rEPV of claim 1 wherein said heterologous gene encodes T7 RNA polymerase.

4. The rePV of claim 3 further comprising a further heterologous gene operatively linked to the T7 RNA polymerase.

5. The rEPV of claim 3 further comprising a temperature or chemically sensitive transcriptional repressor.

6. A composition comprising the rEPV of claim 1 and a carrier.

7. A recombinant entomopoxvirus(rEPV) comprising an early vaccinia virus gene promoter operatively linked to a heterologous gene.

8. The rEPV of claim 7 wherein said promoter is a natural or synthetic vaccinia virus early gene promoter.

9. The rEPV of claim 7 further comprising a nuclear localization signal directing translocation of said rEPV into a vertebrate cell nucleus.

10. The rEPV of claim 9 further comprising sequences homologous to sequences present at a desired site of homologous recombination within the genonie of said vertebrate cell such that integration of said heterologous gene into said genome is effected.

11. The rEPV of claim 7 wherein said heterologous gene encodes T7 RNA polymerase.

12. The rEPV of claim 11 further comprising a further heterologous gene operatively linked to the T7 RNA polymerase.

13. The rEPV of claim 11 further comprising a temperature or chemically sensitive transcriptional repressor.

14. A method for delivering a heterologous gene to a vertebrate cell comprising contacting the vertebrate cell with a recombinant entomopoxvirus (rEPV) encoding said heterologous gene operatively linked to:

(a) an early poxvirus promoter recognized by entomopoxvirus transcriptional factors present in an entomopoxvirus viral particle and recognized by vertebrate transcriptional factors;

(b) a late entomopoxvirus gene promoter, wherein said vertebrate cell is co-infected with a vaccinia virus; or (c) an early vaccinia virus gene promoter; and delivering said heterologous gene to said vertebrate cell, wherein said heterologous gene is expressed by said vertebrate cell.

15. The method of claim 14 wherein said promoter is an early entomopoxvirus gene promoter.

16. the method of claim 14 wherein said promoter is the EPV 42k gene promoter, the EPV fusolin gene promoter, a synthetic entomopoxvirus early gene promoter or a synhetic vaccinia virus early gene promoter.

17. The method of claim 14 wherein said contacting occurs in vivo.

18. The method of claim 14 wherein said contacting occurs in vitro.

19. The method of claim 14 wherein said contacting occurs by introducing said rEPV directly into an organ of said vertebrate.

20. The method of claim 14 wherein said rEPV contains the bacteriophage T7 promoter.

21. The method of claim 14 wherein said rEPV encodes a nuclear localization signal.

22. An isolated vertebrate cell expressing a heterologous gene encoded by a recombinant entomopoxvirus (rEPV) comprising an early entomopoxvirus gene promoter, an early vaccinia virus gene promoter or an early poxvirus promoter recognized by vertebrate transcriptional factors, wherein said promoter is operatively linked to said heterologous gene.

23. A system for delivering a heterologous gene to a vertebrate cell for expression which comprises a recombinant entomopoxvirus (rEPV) and a vaccinia virus, wherein said rEPV comprises;

said heterologous gene operativelv linked to a late entomopoxvirus promoter and further comprising a nuclear localization signal.

24. An isolated vertebrate cell expressing a heterologous gene encoded by a recombinant entomopoxvirus (rEPV), wherein said cell is co-infected by a vaccinia virus, and wherein said rEPV comprises a late entomopoxvirus promoter operatively linked to a heterologous gene.

25. The isolated vertebrate cell of claim 24 wherein said vaccinia virus is a replication deficient vaccinia virus.

* * * * *

UNITED STATES PATENT AND TRADEMARK OFFICE

CERTIFICATE OF CORRECTION

PATENT NO. : 6,106,825
DATED : August 25, 2000
INVENTOR(S) : Richard W. Moyer, Yi Li, Richard L. Hall It is certified that error appears in the above-identified patent and that said Letters Patent is hereby corrected as shown below:

Column 1,
Line 46, "fromAmsacta" should read -- from Amsacta --.
Line 56, "AMEPV" should read -- AmEPV --.

Column 2,
Line 16, "AMEPV" should read -- AmEPV --.

Column 5,
Line 10, "AMEPV" should read -- AmEPV --.

Column 6,
Line 32, "AMEPV" should read -- AmEPV --.
Line 52, "AMEPV" should read -- AmEPV --.
Line 63, "AMEPV" should read -- AmEPV --.

Column 9,
Line 62, "anti-p" should read -- anti-β --.

Column 10,
Line 53, "TFN,IL-1" should read -- TFN, IL-1 --.

Column 11,
Lines 26-27, "0.1 $\mu$mg/kg to 10 $\mu$/kg." should read -- 0.1 $\mu$g/kg to 10 $\mu$g/kg. --.

Column 12,
Line 29, "for8" should read -- for 8 --.
Line 55, "HindII" should read -- *Hind*III --.

Column 13,
Line 66, "RM 548" should read -- RM548 --.

Column 14,
Line 33, "40C" should read -- 40°C --.

UNITED STATES PATENT AND TRADEMARK OFFICE
CERTIFICATE OF CORRECTION

PATENT NO. : 6,106,825
DATED : August 25, 2000
INVENTOR(S) : Richard W. Moyer, Yi Li, Richard L. Hall It is certified that error appears in the above-identified patent and that said Letters Patent is hereby corrected as shown below:

Column 16,
Line 7, "IF" should read -- 1F --.

Column 36,
Line 55, "rePV" should read -- rEPV --.

Column 37,
Line 32, "the method" should read -- The method --.
Line 34, "synhetic" should read -- synthetic --.

Signed and Sealed this

Twenty-third Day of October, 2001

*Attest:*

Nicholas P. Godici

NICHOLAS P. GODICI

*Attesting Officer* *Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:1:

ACAGGAGCTC GCTATTATAA CTAATGTGAG 30

(2) INFORMATION FOR SEQ ID NO:2:

(i) SEQUENCE CHARACTERISTICS:
(A) LENGTH: 30 base pairs
(B) TYPE: nucleic acid

-continued (C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:2:

CACAGGATCC GTTGCTAAAG GTACGTTACT 30

(2) INFORMATION FOR SEQ ID NO:3:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:3:

AGAGAAGCTT CAGCCCAGAT ACTACGATTC 30

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:4:

CACAGTTAAC ACACTTGATG CAACTCTAGC 30

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:5:

ACAGGAGCTC GAATTCAAGT TAAATATTTA 30

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: both
(D) TOPOLOGY: both -continued (iii) HYPOTHETICAL: NO (iv) ANTI-SENSE: NO (xi) SEQUENCE DESCRIPTION: SEQ ID NO:6:

CACAGGATCC CTGGCAAAAC AACAGAATTG 30

(2) INFORMATION FOR SEQ ID NO:7:

(i) SEQUENCE CHARACTERISTICS:
(A) LENGTH: 31 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:7:

AGAGAAGCTT CAAAATGGAT TTACTAAATT C 31

(2) INFORMATION FOR SEQ ID NO:8:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:8:

CACAGTTAAC GAATTCATAT TCAATTATAT 30

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:9:

ACAGGATCCG TACGTATATT AATCATGATT 30

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO -continued (xi) SEQUENCE DESCRIPTION: SEQ ID NO:10:

GACCCATGGT AAAGATCTTT GGTAATAATA 30

(2) INFORMATION FOR SEQ ID NO:11:

(i) SEQUENCE CHARACTERISTICS:
(A) LENGTH: 4810 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:11:

GAGCTCGAAT TCAAGTTAAA TATTTATAAA CAACAATCAT ATTTTTTTAA AGAATCTAAT 60

AAATTTTTTA ACATTTTATT ATTATTTGAT AATTGTTTAT TTAATTCGTT ATTGATATTA 120

ACAATATTAT TTATCATTTT ACCTATTTTT TTTTTTCTAT CTACTAACGA AATATCAGAT 180

TTTGCACCTT CAATATCAGA ATAATAATTA TCATTATTTT GCATTTATGA ATAAAAATAT 240

TAATATGAAT TATTATAACA TAATCTACAC ACAGGAACAT ATAAATCTTG TCCACCTATT 300

TCAATTATTT GATTTTTATT ATGTTTTTTA ATTGTAAAAG AAGCATCTTT ATAACAAAAT 360

TGACATATAG CTTGTAATTT TTTTATTTTT TCTACTTTAG GAATTAATTT TGATATAGAA 420

TTAAATATAT TTCTGTTAAA GTCACAATTT AATCCAGCAA CAATAACTTT TTTTTTATTA 480

TTAGCCATTT TATCACAAAA TTGTTCTAAA TCATTTTCTT CAAAAAATTG ACACTCATCT 540

ATGCCAATAA TATCATAATT ATCTACGATA TTGATTTCAT TAATTAAATT ATTTGTTTTA 600

ATGTATAAAT ATTCTTTATT TAATATATTT CCGTCATGAT TTATTATATT TTTATTTATA 660

AATCTATTAT CTATATTATG AGTTATAATT ACACATTTTT GATTAGATAA AATATATCTA 720

TTAATTTTTC GCATCAATTC TGTTGTTTTG CCAGGGATCC GTACGTATAT TAATCATGAT 780

TGGATAAATA TATTTGAAAA AATTGAATTA TTAAAAAATA ATAAAAAAAA TTATATTGAT 840

GATTATTGGA TCAAACAATC TTCTTTAGAT GATTTATTAT TATATATATC AAATAAAGAA 900

ACTAATGTAT AATATATTTT TATTATATAG ATATTTTTAT AAATAATAAA TTTATTGAAT 960

GAAAAATAAG TATTAGAAAT TAAAATACTC ACAAATTCAG TTCCTATTAT TACCAAAGAT 1020

CTTTACCATG GGGGATCCCG TCGTTTTACA ACGTCGTGAC TGGGAAAACC CTGGCGTTAC 1080

CCAACTTAAT CGCCTTGCAG CACATCCCCC TTTCGCCAGC TGGCGTAATA GCGAAGAGGC 1140

CCGCACCGAT CGCCCTTCCC AACAGTTGCG CAGCCTGAAT GGCGAATGGC GCTTTGCCTG 1200

GTTTCCGGCA CCAGAAGCGG TGCCGGAAAG CTGGCTGGAG TGCGATCTTC CTGAGGCCGA 1260

TACTGTCGTC GTCCCCTCAA ACTGGCAGAT GCACGGTTAC GATGCGCCCA TCTACACCAA 1320

CGTAACCTAT CCCATTACGG TCAATCCGCC GTTTGTTCCC ACGGAGAATC CGACGGGTTG 1380

TTACTCGCTC ACATTTAATG TTGATGAAAG CTGGCTACAG GAAGGCCAGA CGCGAATTAT 1440

TTTTGATGGC GTTAACTCGG CGTTTCATCT GTGGTGCAAC GGGCGCTGGG TCGGTTACGG 1500

CCAGGACAGT CGTTTGCCGT CTGAATTTGA CCTGAGCGCA TTTTTACGCG CCGGAGAAAA 1560

CCGCCTCGCG GTGATGGTGC TGCGTTGGAG TGACGGCAGT TATCTGGAAG ATCAGGATAT 1620

GTGGCGGATG AGCGGCATTT TCCGTGACGT CTCGTTGCTG CATAAACCGA CTACACAAAT 1680

CAGCGATTTC CATGTTGCCA CTCGCTTTAA TGATGATTTC AGCCGCGCTG TACTGGAGGC 1740

-continued

```
TGAAGTTCAG ATGTGCGGCG AGTTGCGTGA CTACCTACGG GTAACAGTTT CTTTATGGCA   1800
GGGTGAAACG CAGGTCGCCA GCGGCACCGC GCCTTTCGGC GGTGAAATTA TCGATGAGCG   1860
TGGTGGTTAT GCCGATCGCG TCACACTACG TCTGAACGTC GAAAACCCGA AACTGTGGAG   1920
CGCCGAAATC CCGAATCTCT ATCGTGCGGT GGTTGAACTG CACACCGCCG ACGGCACGCT   1980
GATTGAAGCA GAAGCCTGCG ATGTCGGTTT CCGCGAGGTG CGGATTGAAA ATGGTCTGCT   2040
GCTGCTGAAC GGCAAGCCGT TGCTGATTCG AGGCGTTAAC CGTCACGAGC ATCATCCTCT   2100
GCATGGTCAG GTCATGGATG AGCAGACGAT GGTGCAGGAT ATCCTGCTGA TGAAGCAGAA   2160
CAACTTTAAC GCCGTGCGCT GTTCGCATTA TCCGAACCAT CCGCTGTGGT ACACGCTGTG   2220
CGACCGCTAC GGCCTGTATG TGGTGGATGA AGCCAATATT GAAACCCACG GCATGGTGCC   2280
AATGAATCGT CTGACCGATG ATCCGCGCTG GCTACCGGCG ATGAGCGAAC GCGTAACGCG   2340
AATGGTGCAG CGCGATCGTA ATCACCCGAG TGTGATCATC TGGTCGCTGG GGAATGAATC   2400
AGGCCACGGC GCTAATCACG ACGCGCTGTA TCGCTGGATC AAATCTGTCG ATCCTTCCCG   2460
CCCGGTGCAG TATGAAGGCG GCGGAGCCGA CACCACGGCC ACCGATATTA TTTGCCCGAT   2520
GTACGCGCGC GTGGATGAAG ACCAGCCCTT CCCGGCTGTG CCGAAATGGT CCATCAAAAA   2580
ATGGCTTTCG CTACCTGGAG AGACGCGCCC GCTGATCCTT TGCGAATACG CCCACGCGAT   2640
GGGTAACAGT CTTGGCGGTT TCGCTAAATA CTGGCAGGCG TTTCGTCAGT ATCCCCGTTT   2700
ACAGGGCGGC TTCGTCTGGG ACTGGGTGGA TCAGTCGCTG ATTAAATATG ATGAAAACGG   2760
CAACCCGTGG TCGGCTTACG GCGGTGATTT TGGCGATACG CCGAACGATC GCCAGTTCTG   2820
TATGAACGGT CTGGTCTTTG CCGACCGCAC GCCGCATCCA GCGCTGACGG AAGCAAAACA   2880
CCAGCAGCAG TTTTTCCAGT TCCGTTTATC CGGGCAAACC ATCGAAGTGA CCAGCGAATA   2940
CCTGTTCCGT CATAGCGATA ACGAGCTCCT GCACTGGATG GTGGCGCTGG ATGGTAAGCC   3000
GCTGGCAAGC GGTGAAGTGC CTCTGGATGT CGCTCCACAA GGTAAACAGT TGATTGAACT   3060
GCCTGAACTA CCGCAGCCGG AGAGCGCCGG GCAACTCTGG CTCACAGTAC GCGTAGTGCA   3120
ACCGAACGCG ACCGCATGGT CAGAAGCCGG GCACATCAGC GCCTGGCAGC AGTGGCGTCT   3180
GGCGGAAAAC CTCAGTGTGA CGCTCCCCGC CGCGTCCCAC GCCATCCCGC ATCTGACCAC   3240
CAGCGAAATG GATTTTTGCA TCGAGCTGGG TAATAAGCGT TGGCAATTTA ACCGCCAGTC   3300
AGGCTTTCTT TCACAGATGT GGATTGGCGA TAAAAAACAA CTGCTGACGC CGCTGCGCGA   3360
TCAGTTCACC CGTGCACCGC TGGATAACGA CATTGGCGTA AGTGAAGCGA CCCGCATTGA   3420
CCCTAACGCC TGGGTCGAAC GCTGGAAGGC GGCGGGCCAT TACCAGGCCG AAGCAGCGTT   3480
GTTGCAGTGC ACGGCAGATA CACTTGCTGA TGCGGTGCTG ATTACGACCG CTCACGCGTG   3540
GCAGCATCAG GGGAAAACCT TATTTATCAG CCGGAAAACC TACCGGATTG ATGGTAGTGG   3600
TCAAATGGCG ATTACCGTTG ATGTTGAAGT GGCGAGCGAT ACACCGCATC CGGCGCGGAT   3660
TGGCCTGAAC TGCCAGCTGG CGCAGGTAGC AGAGCGGGTA AACTGGCTCG GATTAGGGCC   3720
GCAAGAAAAC TATCCCGACC GCCTTACTGC CGCCTGTTTT GACCGCTGGG ATCTGCCATT   3780
GTCAGACATG TATACCCCGT ACGTCTTCCC GAGCGAAAAC GGTCTGCGCT GCGGGACGCG   3840
CGAATTGAAT TATGGCCCAC ACCAGTGGCG CGGCGACTTC CAGTTCAACA TCAGCCGCTA   3900
CAGTCAACAG CAACTGATGG AAACCAGCCA TCGCCATCTG CTGCACGCGG AAGAAGGCAC   3960
ATGGCTGAAT ATCGACGGTT TCCATATGGG GATTGGTGCG GACGACTCCT GGAGCCCGTC   4020
AGTATCGGCG GAATTCCAGC TGAGCGCCGG TCGCTACCAT TACCAGTTGG TCTGGTGTCA   4080
```

-continued

```
AAAATAATAA TAACCGGGCA GGGGGGATCC GTCGACCTGC AGGAATTCGA TATCAAGCTT   4140

CAAAATGGAT TTACTAAATT CTGATATAAT TTTAATAAAT ATTTTAAAAT ATTATAATTT   4200

AAAAAAAATA ATAATAAACA GAGATAATGT TATTAATATT AATATATTAA AAAAATTAGT   4260

TAATTTAGAA GAATTGCATA TAATATATTA TGATAATAAT ATTTTAAATA ATATTCCAGA   4320

AAATATTAAA AGTTTATATA TTTCAAATTT AAATATTATT AATTTAAATT TTATAACAAA   4380

ATTAAAAAAT ATAACATATT TAGATATATC TTATAACAAA AATAGCAATA TAAGTAATAT   4440

TATACTACCA CATTCTATAG AATTTTTAAA TTGTGAATCA TGTAATATAA ATGACTATAA   4500

TTTTATTAAT AATTTAGTAA ATTTAAAAAA ATTAATAATA TCTAAAAATA AATTTGGTAA   4560

CTTTAATAAT GTTTTTCCTA TTAGTATAGT TGAGTTAAAT ATGGAATCAA TACAAATAAA   4620

AGATTATAAA TTTATAGAAA AATTAATTAA TTTAAAAAAA TTAGATATAT CTTTCAATGT   4680

TAAAAAAAAT AATATACATT TGATAAAATT TCCAAAAAGT ATAACTCATT TATGTGATTA   4740

TCAATCATAT AAAGAAAATT ATAATTATTT AAAAAATTTA TCAAATATAA TTGAATATGA   4800

ATTCGTTAAC                                                          4810
```

(2) INFORMATION FOR SEQ ID NO:12:

(i) SEQUENCE CHARACTERISTICS:
(A) LENGTH: 24 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:12:

```
TCAAAAAAAT ATAAATGATT CACC                                            24
```

(2) INFORMATION FOR SEQ ID NO:13:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:13:

```
GACCCATGGC GATTTTATAT TGTAATTATA                                      30
```

(2) INFORMATION FOR SEQ ID NO:14:

(i) SEQUENCE CHARACTERISTICS:
(A) LENGTH: 30 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO -continued (xi) SEQUENCE DESCRIPTION: SEQ ID NO:14:

ACAAGATCTA TAATAATGTA AAATCGCAGT 30

(2) INFORMATION FOR SEQ ID NO:15:

(i) SEQUENCE CHARACTERISTICS:
(A) LENGTH: 4838 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:15:

GAGCTCGAAT TCAAGTTAAA TATTTATAAA CAACAATCAT ATTTTTTTAA AGAATCTAAT 60

AAATTTTTTA ACATTTTATT ATTATTTGAT AATTGTTTAT TTAATTCGTT ATTGATATTA 120

ACAATATTAT TTATCATTTT ACCTATTTTT TTTTTTCTAT CTACTAACGA AATATCAGAT 180

TTTGCACCTT CAATATCAGA ATAATAATTA TCATTATTTT GCATTTATGA ATAAAAATAT 240

TAATATGAAT TATTATAACA TAATCTACAC ACAGGAACAT ATAAATCTTG TCCACCTATT 300

TCAATTATTT GATTTTTATT ATGTTTTTTA ATTGTAAAAG AAGCATCTTT ATAACAAAAT 360

TGACATATAG CTTGTAATTT TTTTATTTTT TCTACTTTAG GAATTAATTT TGATATAGAA 420

TTAAATATAT TTCTGTTAAA GTCACAATTT AATCCAGCAA CAATAACTTT TTTTTTATTA 480

TTAGCCATTT TATCACAAAA TTGTTCTAAA TCATTTTCTT CAAAAAATTG ACACTCATCT 540

ATGCCAATAA TATCATAATT ATCTACGATA TTGATTTCAT TAATTAAATT ATTTGTTTTA 600

ATGTATAAAT ATTCTTTATT TAATATATTT CCGTCATGAT TTATTATATT TTTATTTATA 660

AATCTATTAT CTATATTATG AGTTATAATT ACACATTTTT GATTAGATAA AATATATCTA 720

TTAATTTTTC GCATCAATTC TGTTGTTTTG CCAGGGATCC GTACACAAGA TCTATAATAA 780

TGTAAAATCG CAGTTAAAAA CAATTGTATT TAATGAAAAA ACAAGACAAT ATAAAATAGA 840

CGGATTATTT AAAAATTTCA TAATAGACGA AAGTTTTAAA AATATAATAA GTAAATTTAT 900

TAATGATATT CAATGTGTTA TATGCGATCT ATGGTTAACT ATTCAAAAAA ATATAAATGA 960

TTCACCATCT GATAGAAAAA AAATTTATTG GGAACAATAT GATAATATTT TGGGATTTCA 1020

AAATTGAAAA TATATAATTA CAATATAAAA TCGCCATGGG GGATCCCGTC GTTTTACAAC 1080

GTCGTGACTG GGAAAACCCT GGCGTTACCC AACTTAATCG CCTTGCAGCA CATCCCCCTT 1140

TCGCCAGCTG GCGTAATAGC GAAGAGGCCC GCACCGATCG CCCTTCCCAA CAGTTGCGCA 1200

GCCTGAATGG CGAATGGCGC TTTGCCTGGT TTCCGGCACC AGAAGCGGTG CCGGAAAGCT 1260

GGCTGGAGTG CGATCTTCCT GAGGCCGATA CTGTCGTCGT CCCCTCAAAC TGGCAGATGC 1320

ACGGTTACGA TGCGCCCATC TACACCAACG TAACCTATCC CATTACGGTC AATCCGCCGT 1380

TTGTTCCCAC GGAGAATCCG ACGGGTTGTT ACTCGCTCAC ATTTAATGTT GATGAAAGCT 1440

GGCTACAGGA AGGCCAGACG CGAATTATTT TTGATGGCGT TAACTCGGCG TTTCATCTGT 1500

GGTGCAACGG GCGCTGGGTC GGTTACGGCC AGGACAGTCG TTTGCCGTCT GAATTTGACC 1560

TGAGCGCATT TTTACGCGCC GGAGAAAACC GCCTCGCGGT GATGGTGCTG CGTTGGAGTG 1620

ACGGCAGTTA TCTGGAAGAT CAGGATATGT GGCGGATGAG CGGCATTTTC CGTGACGTCT 1680

CGTTGCTGCA TAAACCGACT ACACAAATCA GCGATTTCCA TGTTGCCACT CGCTTTAATG 1740

-continued

```
ATGATTTCAG CCGCGCTGTA CTGGAGGCTG AAGTTCAGAT GTGCGGCGAG TTGCGTGACT   1800
ACCTACGGGT AACAGTTTCT TTATGGCAGG GTGAAACGCA GGTCGCCAGC GGCACCGCGC   1860
CTTTCGGCGG TGAAATTATC GATGAGCGTG GTGGTTATGC CGATCGCGTC ACACTACGTC   1920
TGAACGTCGA AAACCCGAAA CTGTGGAGCG CCGAAATCCC GAATCTCTAT CGTGCGGTGG   1980
TTGAACTGCA CACCGCCGAC GGCACGCTGA TTGAAGCAGA AGCCTGCGAT GTCGGTTTCC   2040
GCGAGGTGCG GATTGAAAAT GGTCTGCTGC TGCTGAACGG CAAGCCGTTG CTGATTCGAG   2100
GCGTTAACCG TCACGAGCAT CATCCTCTGC ATGGTCAGGT CATGGATGAG CAGACGATGG   2160
TGCAGGATAT CCTGCTGATG AAGCAGAACA ACTTTAACGC CGTGCGCTGT TCGCATTATC   2220
CGAACCATCC GCTGTGGTAC ACGCTGTGCG ACCGCTACGG CCTGTATGTG GTGGATGAAG   2280
CCAATATTGA AACCCACGGC ATGGTGCCAA TGAATCGTCT GACCGATGAT CCGCGCTGGC   2340
TACCGGCGAT GAGCGAACGC GTAACGCGAA TGGTGCAGCG CGATCGTAAT CACCCGAGTG   2400
TGATCATCTG GTCGCTGGGG AATGAATCAG GCCACGGCGC TAATCACGAC GCGCTGTATC   2460
GCTGGATCAA ATCTGTCGAT CCTTCCCGCC CGGTGCAGTA TGAAGGCGGC GGAGCCGACA   2520
CCACGGCCAC CGATATTATT TGCCCGATGT ACGCGCGCGT GGATGAAGAC CAGCCCTTCC   2580
CGGCTGTGCC GAAATGGTCC ATCAAAAAAT GGCTTTCGCT ACCTGGAGAG ACGCGCCCGC   2640
TGATCCTTTG CGAATACGCC CACGCGATGG GTAACAGTCT TGGCGGTTTC GCTAAATACT   2700
GGCAGGCGTT TCGTCAGTAT CCCCGTTTAC AGGGCGGCTT CGTCTGGGAC TGGGTGGATC   2760
AGTCGCTGAT TAAATATGAT GAAAACGGCA ACCCGTGGTC GGCTTACGGC GGTGATTTTG   2820
GCGATACGCC GAACGATCGC CAGTTCTGTA TGAACGGTCT GGTCTTTGCC GACCGCACGC   2880
CGCATCCAGC GCTGACGGAA GCAAAACACC AGCAGCAGTT TTTCCAGTTC CGTTTATCCG   2940
GGCAAACCAT CGAAGTGACC AGCGAATACC TGTTCCGTCA TAGCGATAAC GAGCTCCTGC   3000
ACTGGATGGT GGCGCTGGAT GGTAAGCCGC TGGCAAGCGG TGAAGTGCCT CTGGATGTCG   3060
CTCCACAAGG TAAACAGTTG ATTGAACTGC CTGAACTACC GCAGCCGGAG AGCGCCGGGC   3120
AACTCTGGCT CACAGTACGC GTAGTGCAAC CGAACGCGAC CGCATGGTCA GAAGCCGGGC   3180
ACATCAGCGC CTGGCAGCAG TGGCGTCTGG CGGAAAACCT CAGTGTGACG CTCCCCGCCG   3240
CGTCCCACGC CATCCCGCAT CTGACCACCA GCGAAATGGA TTTTTGCATC GAGCTGGGTA   3300
ATAAGCGTTG GCAATTTAAC CGCCAGTCAG GCTTTCTTTC ACAGATGTGG ATTGGCGATA   3360
AAAAACAACT GCTGACGCCG CTGCGCGATC AGTTCACCCG TGCACCGCTG GATAACGACA   3420
TTGGCGTAAG TGAAGCGACC CGCATTGACC CTAACGCCTG GGTCGAACGC TGGAAGGCGG   3480
CGGGCCATTA CCAGGCCGAA GCAGCGTTGT TGCAGTGCAC GGCAGATACA CTTGCTGATG   3540
CGGTGCTGAT TACGACCGCT CACGCGTGGC AGCATCAGGG GAAAACCTTA TTTATCAGCC   3600
GGAAAACCTA CCGGATTGAT GGTAGTGGTC AAATGGCGAT TACCGTTGAT GTTGAAGTGG   3660
CGAGCGATAC ACCGCATCCG GCGCGGATTG GCCTGAACTG CCAGCTGGCG CAGGTAGCAG   3720
AGCGGGTAAA CTGGCTCGGA TTAGGGCCGC AAGAAAACTA TCCCGACCGC CTTACTGCCG   3780
CCTGTTTTGA CCGCTGGGAT CTGCCATTGT CAGACATGTA TACCCCGTAC GTCTTCCCGA   3840
GCGAAAACGG TCTGCGCTGC GGGACGCGCG AATTGAATTA TGGCCCACAC CAGTGGCGCG   3900
GCGACTTCCA GTTCAACATC AGCCGCTACA GTCAACAGCA ACTGATGGAA ACCAGCCATC   3960
GCCATCTGCT GCACGCGGAA GAAGGCACAT GGCTGAATAT CGACGGTTTC CATATGGGGA   4020
TTGGTGCGGA CGACTCCTGG AGCCCGTCAG TATCGGCGGA ATTCCAGCTG AGCGCCGGTC   4080
GCTACCATTA CCAGTTGGTC TGGTGTCAAA AATAATAATA ACCGGGCAGG GGGGATCCGT   4140
```

-continued

```
CGACCTGCAG GAATTCGATA TCAAGCTTCA AAATGGATTT ACTAAATTCT GATATAATTT   4200

TAATAAATAT TTTAAAATAT TATAATTTAA AAAAAATAAT AATAAACAGA GATAATGTTA   4260

TTAATATTAA TATATTAAAA AAATTAGTTA ATTTAGAAGA ATTGCATATA ATATATTATG   4320

ATAATAATAT TTTAAATAAT ATTCCAGAAA ATATTAAAAG TTTATATATT TCAAATTTAA   4380

ATATTATTAA TTTAAATTTT ATAACAAAAT TAAAAAATAT AACATATTTA GATATATCTT   4440

ATAACAAAAA TAGCAATATA AGTAATATTA TACTACCACA TTCTATAGAA TTTTTAAATT   4500

GTGAATCATG TAATATAAAT GACTATAATT TTATTAATAA TTTAGTAAAT TTAAAAAAAT   4560

TAATAATATC TAAAAATAAA TTTGGTAACT TTAATAATGT TTTTCCTATT AGTATAGTTG   4620

AGTTAAATAT GGAATCAATA CAAATAAAAG ATTATAAATT TATAGAAAAA TTAATTAATT   4680

TAAAAAAATT AGATATATCT TTCAATGTTA AAAAAAATAA TATACATTTG ATAAAATTTC   4740

CAAAAAGTAT AACTCATTTA TGTGATTATC AATCATATAA AGAAAATTAT AATTATTTAA   4800

AAAATTTATC AAATATAATT GAATATGAAT TCGTTAAC                           4838
```

```
(2) INFORMATION FOR SEQ ID NO:16:

     (i) SEQUENCE CHARACTERISTICS:
          (A) LENGTH: 25 base pairs
          (B) TYPE: nucleic acid
          (C) STRANDEDNESS: both
          (D) TOPOLOGY: both

    (ii) MOLECULE TYPE: cDNA

   (iii) HYPOTHETICAL: NO

    (iv) ANTI-SENSE: NO

    (xi) SEQUENCE DESCRIPTION: SEQ ID NO:16:

AGTCTCATGA GCAAGGGCGA GGAAC                                           25
```

```
(2) INFORMATION FOR SEQ ID NO:17:

     (i) SEQUENCE CHARACTERISTICS:
          (A) LENGTH: 30 base pairs
          (B) TYPE: nucleic acid
          (C) STRANDEDNESS: both
          (D) TOPOLOGY: both

    (ii) MOLECULE TYPE: cDNA

   (iii) HYPOTHETICAL: NO

    (iv) ANTI-SENSE: NO

    (xi) SEQUENCE DESCRIPTION: SEQ ID NO:17:

ACCCAAGCTT CCGCGGCCGC TCACTTGTAC                                      30
```